United States Patent
Flickinger et al.

(10) Patent No.: US 9,788,972 B2
(45) Date of Patent: Oct. 17, 2017

(54) INTER-VERTEBRAL IMPLANT FOR SPINAL FUSION

(71) Applicant: Meditech Spine, LLC, Atlanta, GA (US)

(72) Inventors: Eric Flickinger, Atlanta, GA (US); Bruce Dunaway, Akron, OH (US); Jason J. Gromek, Brecksville, OH (US)

(73) Assignee: MEDITECH SPINE, LLC, Atlanta, GA (US)

( * ) Notice: Subject to any disclaimer, the term of this patent is extended or adjusted under 35 U.S.C. 154(b) by 0 days.

(21) Appl. No.: 15/149,017

(22) Filed: May 6, 2016

(65) Prior Publication Data

US 2016/0324653 A1 Nov. 10, 2016

Related U.S. Application Data

(60) Provisional application No. 62/158,429, filed on May 7, 2015.

(51) Int. Cl.
*A61F 2/44* (2006.01)
*A61F 2/28* (2006.01)
*A61F 2/30* (2006.01)

(52) U.S. Cl.
CPC .......... *A61F 2/447* (2013.01); *A61F 2/2846* (2013.01); *A61F 2/30771* (2013.01); *A61F 2/4455* (2013.01); *A61F 2002/285* (2013.01); *A61F 2002/30904* (2013.01); *A61F 2002/30906* (2013.01); *A61F 2002/4475* (2013.01)

(58) Field of Classification Search
CPC .... A61F 2/447; A61F 2/2846; A61F 2/30771; A61F 2002/285; A61F 2002/30906; A61F 2002/4475; A61F 2002/30904
See application file for complete search history.

(56) References Cited

U.S. PATENT DOCUMENTS

| | | | | |
|---|---|---|---|---|
| 4,834,757 | A | * | 5/1989 | Brantigan .......... A61B 17/1604 623/17.11 |
| 5,554,191 | A | * | 9/1996 | Lahille ............... A61B 17/1757 411/55 |
| 5,609,636 | A | | 3/1997 | Kohrs et al. |
| 6,059,829 | A | * | 5/2000 | Schlapfer ................ A61F 2/447 606/247 |
| 6,371,988 | B1 | * | 4/2002 | Pafford .............. A61B 17/1671 606/247 |

(Continued)

OTHER PUBLICATIONS

International Search Report in Related PCT Application PCT/US2016/031338 dated Aug. 22, 2016, 5 pages.

(Continued)

*Primary Examiner* — Ellen C Hammond
(74) *Attorney, Agent, or Firm* — Kilpatrick Townsend & Stockton LLP

(57) ABSTRACT

An intervertebral implant for supporting vertebrae that includes an anterior end element, a posterior end element, and four wings disposed between the anterior end element and the posterior end element. The four wings and the anterior and posterior end elements define a substantially open central space. The wings are arranged in pairs facing in opposed directions and include teeth facing in those opposed directions for gripping substantially planar surfaces at opposite sides of the implant.

27 Claims, 24 Drawing Sheets

(56) References Cited

U.S. PATENT DOCUMENTS

| | | | |
|---|---|---|---|
| 6,371,989 B1* | 4/2002 | Chauvin | A61F 2/30744 623/17.11 |
| 6,569,201 B2* | 5/2003 | Moumene | A61F 2/447 606/247 |
| 6,610,089 B1* | 8/2003 | Liu | A61B 17/025 623/16.11 |
| 6,743,255 B2* | 6/2004 | Ferree | A61F 2/30742 623/17.11 |
| 7,232,463 B2* | 6/2007 | Falahee | A61B 90/92 623/17.11 |
| 7,794,500 B2 | 9/2010 | Felix | |
| 7,828,848 B2* | 11/2010 | Chauvin | A61F 2/4455 606/313 |
| 9,198,774 B2* | 12/2015 | Pisharodi | A61F 2/447 |
| 9,351,848 B2* | 5/2016 | Glerum | A61F 2/442 |
| 9,414,934 B2* | 8/2016 | Cain | A61F 2/442 |
| 9,456,903 B2* | 10/2016 | Glerum | A61F 2/447 |
| 2002/0068976 A1* | 6/2002 | Jackson | A61F 2/4455 623/17.15 |
| 2002/0068977 A1* | 6/2002 | Jackson | A61F 2/4455 623/17.15 |
| 2002/0128713 A1* | 9/2002 | Ferree | A61F 2/30742 623/17.11 |
| 2002/0143401 A1* | 10/2002 | Michelson | A61F 2/446 623/17.16 |
| 2003/0139812 A1* | 7/2003 | Garcia | A61B 17/1671 623/17.11 |
| 2005/0021144 A1* | 1/2005 | Malberg | A61F 2/4455 623/17.11 |
| 2006/0089716 A1 | 4/2006 | Felix | |
| 2006/0217806 A1* | 9/2006 | Peterman | A61F 2/4455 623/17.11 |
| 2010/0185291 A1* | 7/2010 | Jimenez | F16C 11/12 623/17.16 |
| 2012/0109305 A1* | 5/2012 | Park | A61F 2/442 623/17.13 |
| 2012/0253406 A1* | 10/2012 | Bae | A61F 2/447 606/279 |
| 2013/0166030 A1* | 6/2013 | Biedermann | A61F 2/442 623/17.16 |
| 2014/0277477 A1* | 9/2014 | Malandain | A61F 2/442 623/17.16 |
| 2016/0030194 A1* | 2/2016 | Ledet | A61F 2/44 623/17.16 |
| 2016/0135960 A1* | 5/2016 | Grotz | A61F 2/4637 623/17.16 |

OTHER PUBLICATIONS

Written Opinion in Related PCT Application PCT/US2016/031338 dated Aug. 22, 2016, 5 pages.

* cited by examiner

INTER-VERTEBRAL IMPLANT FOR SPINAL FUSION

CROSS-REFERENCE TO RELATED APPLICATION

This application claims the benefit of U.S. Provisional Application No. 62/158,429 for "Inter-Vertebral Implant For Spinal Fusion" filed May 7, 2015, which is incorporated in this application in its entirety by this reference.

BACKGROUND

Spinal fusion is a surgical technique used to join two or more vertebrae for the correction of various conditions, such as back pain caused by degenerative conditions, misalignment, scoliosis, injury causing misalignment, or abnormal intervertebral motion. Spinal fusion may be indicated for the cervical region or, (more rarely,) the thoracic or lumbar regions.

Spinal fusion, and particularly intervertebral (or interbody) fusion, is accomplished by immobilizing vertebrae relative to one another with one or more surgical implants, removing a portion of material between the vertebrae, and providing graft material between the vertebrae. The material removed typically includes the intervertebral disk, but may often include part(s) of one or both of the adjacent vertebrae. Graft material typically includes supplementary bone material, which may be obtained from the recipient, from a donor, a synthetic substitute, or any suitable combination of the above.

Successful fusion requires that the relative orientation of the fused vertebrae be maintained, as well as the spacing between them. Although the vertebrae may be fixed by mechanical implants, such as rods, plates, or cages connected to the vertebrae by screws, or by exterior support in the form of orthotic bracing, these approaches provide only a limited degree of compressive support to the spine.

BRIEF SUMMARY

The following presents a simplified summary of some embodiments of the invention to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Disclosed is an intervertebral implant, which can include an anterior end element having a widening cross-sectional area in a direction from an anterior end of the implant toward a posterior end along a central axis (or longitudinal axis) of the implant, four wings extending from the anterior end element in the direction of the posterior end and generally parallel to the central axis, and a posterior end element connected to the four wings. The four wings can be arranged in two opposed pairs of adjacent wings, the pairs each having surface features such as teeth and grooves configured to abut two opposed planes, the opposed planes being parallel to a third plane containing the central axis of the implant. The anterior and posterior elements and the wings can define a substantially open space within the implant, and a rear-facing element extending from the anterior end element may be arranged within the substantially open space. The rear-facing element can decrease in cross sectional area from where it joins the anterior end element in the direction of the posterior end of the implant, terminating at a minimum cross-sectional area within the open central space. The rear-facing element can be any suitable shape for directing flow of graft material, e.g., a cone, pyramid, wedge, divider, or other suitable shape.

The intervertebral implants can also include support members between either or both of the anterior and posterior end elements and each one of the four wings. The support members are arranged to act as cantilevered springs, allowing the wings to flex slightly under load. In some intervertebral implants, the widening cross-sectional area of the anterior end element can partially or fully obviate the support members at the anterior end only. The intervertebral implants can also include an arced structure of the wings. For example, each wing can include an arc defined by the peaks of the teeth, each arc being convex in a direction away from a plane containing the central axis of the implant. Under load, the wings can bend from the arced configuration toward a planar configuration.

The intervertebral implants can also include porous or textured surfaces or sections. For example, all or parts of the wings, surface features, support members, and/or posterior and anterior end elements may include surface texturing, a porous lattice, or both. The porous lattice may penetrate to a depth in the implant, such that a portion of the implant remains nonporous for providing structure, while another portion of the implant is porous for enhancing bone ingrowth. In some cases, each wing of an implant may be formed entirely of a porous lattice, or all of or substantially all of the implant may be formed of a porous lattice. For example, an intervertebral implant can have a solid anterior end element and posterior element, and porous wings and support members.

The intervertebral implants, or a portion of the implants including the wings and/or the support members, can be formed of a memory shape material such as a memory shape alloy. Implants formed of memory shape material may be formed in an elevated (or relaxed) state and then collapsed in a plastic-deformation regime, for example at a low temperature. Implants in the collapsed state can have a low thickness compared to implants in the elevated state, and therefore may be easier to install. Implants formed of memory-shape material may subsequently be expanded upon installation by heating the implants above a transition temperature.

The various intervertebral implants disclosed herein may be used for any interbody spinal fusion. Specific examples disclosed herein include implants with particular utility for specific types of interbody spinal fusion. Various exemplary implants include features for aiding installation by way of, e.g., posterior lumber interbody fusion (PLIF), anterior lumber interbody fusion (ALIF), transforaminal lumber interbody fusion (TLIF), lateral lumber interbody fusion (LLIF), and anterior cervical interbody fusion (ACIF), although variations may be adapted for other spinal fusion applications.

For a fuller understanding of the nature and advantages of the present invention, reference should be made to the ensuing detailed description and accompanying drawings.

BRIEF DESCRIPTION OF THE DRAWINGS

These and other features, embodiments, and advantages of the present disclosure are better understood when the following Detailed Description is read with reference to the accompanying drawings.

DETAILED DESCRIPTION

Figure 1:
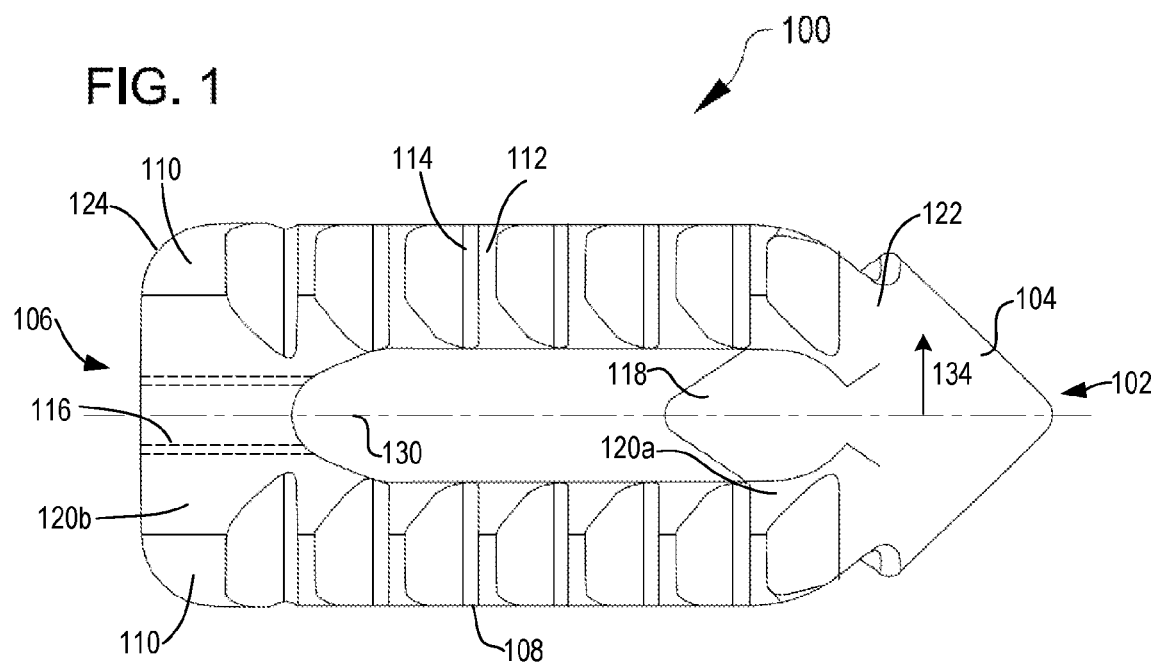
FIGS. 1-5 show one example of an intervertebral fusion implant having a rounded conical anterior end element in various views, including: a top view (FIG. 1), a perspective view (FIG. 2), a posterior view (FIG. 3), a side view (FIG. 4) and an anterior view (FIG. 5)

In the following description, various embodiments of the present invention will be described. For purposes of explanation, specific configurations and details are set forth to provide a thorough understanding of the embodiments. However, it will also be apparent to one skilled in the art that the present invention may be practiced without the specific details. Furthermore, well-known features may be omitted or simplified in order not to obscure the embodiment being described. Directional references such as "up," "down," "top," "bottom," "left," "right," "front," "back," "outer," "inner," and "corners," among others, are intended to refer to the orientation as illustrated and described in the figure (or figures) to which the components and directions are referencing.

The disclosed intervertebral fusion implants have anterior and posterior ends and top and bottom surfaces with surface features configured to grip adjacent vertebral faces while providing access for graft material to join with both adjacent vertebral faces. In some cases, the implants may be inserted into an intervertebral space anterior-end first. In some examples, the anterior end element and the top and bottom surface features may be configured to promote smooth insertion while opposing backout, for example, by way of a wedge-, pyramid-, or cone-shaped (or other suitable shape) anterior end element and directional teeth, fins or notches in the surface features. The supporting structures of the implant are shaped to permit limited elastic deformation while also providing abundant open space for graft material to interfuse with both vertebral faces. For example, supporting structures may include 'X'-shaped (or other shaped) connections from the anterior and posterior ends of the implants to the wings, the connections being configured to deform slightly when the wings are loaded. In some cases, supporting structures may originate internally, e.g., from a portion of the implant between the anterior and posterior ends. The implant may also provide internal features for introducing and diffusing the graft material.

In addition, the implant may be made of a material having higher or significantly higher stiffness than bone, in contrast to conventional implants formed of stiff plastic such as PEEK, due to the supporting structure being configured to provide spring-like elastic deformation for providing more bone-like macro-scale stiffness in the structure of the implant as a whole. By way of example, the supporting structure may include substantially cantilevered structural elements that can bend elastically even when the supporting structure as a whole is formed of a material much stiffer than bone. The intervertebral fusion implants may be made of titanium or titanium alloy, or any other suitable medical-grade alloy. Suitable materials may include, but are not limited to, titanium alloys Ti-6Al-4V, Ti-6Al-4V ELI, or Ti-6Al-7Nb, cobalt-chrome alloys, Cobalt-chrome-molybdenum alloys, any suitable low-nickel metal orthopedic alloy with high biocompatibility, or any other suitable high-strength biocompatible material. In some cases, the implant may be made of PEEK or other suitable plastic.

Alternatively, the implant may be made of an adaptive material that changes in stiffness depending on applied load or cycling applied load over time. In some examples, an adaptive material may have a yield strength on the order of 400-500 MPa, comparable to some grades of titanium, but possess a stiffness on the order of 10-30 GPa, which is on the order of between $\frac{1}{10}$th to $\frac{1}{3}$rd of the stiffness of a conventional titanium implant, or on the order of $\frac{1}{20}$th to $\frac{1}{6}$th of the stiffness of a conventional cobalt-chrome medical alloy. In some cases, the stiffness of an adaptive alloy may vary from a high value to a low value depending on applied stress, where the range of variance may be approximately less than 100 Gpa to more than 10 GPa (or 10-100 GPa), 20-65 GPa, or 20-55 GPa. A non-limiting example of a suitable adaptive material may be a metastable Titanium-Molybdenum alloy such as a β-type Ti-16Mo alloy or any other suitable metastable medical-grade alloy.

Alternatively, the implant may be made from a shape-memory material, such as the shape-memory alloy nickel titanium (TiNi, or nitinol), which may undergo deformation at one range of temperatures and recover an original, undeformed shape when returned above a transition temperature. Implants formed of a shape-memory material may be deformed to a compressed configuration at a plastic deformation regime, so that they can be inserted in a patient while compressed, and subsequently return to an expanded (or uncompressed) configuration after being surgically positioned at a therapeutic site. In some cases, where the transition temperature is below the resting temperature of the human body, the implant may return to its expanded shape in response to warming from the patient's body. In other examples, where the transition temperature is higher than the resting temperature of the human body, the implant may be returned to its expanded shape by a practitioner supplying an external heat source to the implant during installation.

The disclosed implants may be formed by any suitable manufacturing process, such as machining. The manufacturing process may be a form of 3D printing or solid freeform fabrication technique, for example, selective laser sintering (SLS), selective laser melting (SLM), electron-beam melting (EBM), or other suitable powder bed fusion technique, or any suitable additive manufacturing technique. The implant may be formed in a single operation, or in multiple operations. The implant may be formed as a contiguous part or may be formed of more than one part joined together, for example, by additive manufacturing, welding, mechanical attachment, or any other suitable means of joining.

The implants may include one or more substantially porous or textured sections, for encouraging optimal bone ingrowth with the implant. For example, the outer surfaces of the wings, inclusive of the teeth or other surface feature (s), may include a rough, grooved, porous, or otherwise textured surface. The textured surface may be formed by a surface treatment, such as machining, plasma treatment, deposition of material, or other treatment. The textured surface may alternatively be formed in the initial manufacture of the implant, for example, during any suitable additive manufacturing technique as described above. Any suitable portion of the implant may include the porous section(s). In some cases, the porous section may include all or part of the wings, and/or all or part of the supporting structures connecting the wings to the anterior and posterior ends of the implant, and/or all or part of both or either of the anterior and posterior end elements of implant. In some cases, a portion of each wing is substantially porous, and a portion of each wing is nonporous, resulting in a hybrid structure having good surface porosity for bone ingrowth as well as predictable load-bearing properties from the nonporous structural sections. For example, in an implant having teeth in the surfaces of the wings, the teeth may be porous from a tip to a depth of approximately 2-3 mm, and the remainder of the teeth and underlying wing may be nonporous. A porous section may include a porous lattice with unique, patterned, or random voids, and void sizes may be uniform or vary substantially, inclusive of void sizes smaller than or up to the orders of microns, tens of microns, hundreds of microns, and millimeters.

Referring now to the drawings, in which like reference numerals represent like parts throughout the several views, FIG. 1 shows an intervertebral fusion implant 100 having a rounded conical anterior end element 102 in a top view. The tip of the rounded conical anterior end element 102 defines a central axis 130 (or longitudinal axis) of the implant 100, and an anterior cone 104 expands from the conical anterior end element 102 toward a posterior end 106. The anterior cone 104 (FIG. 4) may increase in size (e.g., in horizontal and vertical directions 134, 132 (FIGS. 1 and 4)) from a minimum size at the tip of the anterior end element 102 to a maximum at anterior shoulders 122. Four wings 108 extend between the anterior end element 102 and a posterior end 106 of the implant 100. Structural members 120a connect a first end of each of the wings 108 with the anterior end element 102 of the implant 100, while structural members 120b connect a second end (opposite the first end) of each of the wings 108 with the posterior end 106 of the implant 100. Structural members 120a, 120b may include the anterior shoulders 122 and posterior shoulders 124, respectively. The wings 108, anterior end element 102, and posterior end 106 define an open space therebetween along the central axis 130.

The wings 108 possess anti-migratory features such as teeth 112 and grooves 114 on outer (top and/or bottom) surfaces 110. In some cases, the top and/or bottom surfaces may be oriented interchangeably when inserted into a patient. Adjacent wings 108 (e.g., two top wings or two bottom wings) are aligned facing the same direction. The outer surfaces 110 of the wings 108 may originate from a curved surface defined by an arc 126 (see FIG. 4). The outer surface 110 and the teeth 112 of the wings 108 may define a curved profile of the arc 126 (see FIG. 4), originating at curved anterior shoulder 122 and terminating at curved posterior shoulder 124. The outer surface 110 may be curved where it terminates at the posterior shoulder 124. The wings may have stiffness such that the curved profile may flatten into a planar or substantially planar profile when the implant 100 is placed under an axial load.

Alternatively, where the wings 108 and structural members 120a, 120b are formed of a shape-memory alloy, the wings 108 and structural members 120a, 120b may be configured to plastically bend into a compressed shape with a low profile for installation, and to revert to a therapeutically optimal size after installation. For example, a shape-memory implant may have a recovery temperature at or below the temperature of the human body, and may be cooled and deformed to a compressed shape prior to surgical installation. In the compressed shape, the wings 108 of the implant 100 may be bent toward a plane that passes through the central axis 130, such that opposed wings (e.g., a top wing and a bottom wing) are closer together and adjacent wings (e.g., two top wings or two bottom wings) are farther apart. The implant may be kept below its transition temperature until immediately before installation, and allowed to expand in place once inserted into the intervertebral space.

The posterior end 106 of the implant 100, where the posterior structural members 120b join, may be a substantially cylindrical structure having a hollow portion forming a cylindrical cavity 116. The cavity 116 is configured to permit the insertion of graft material therethrough such that the graft material may be forced through the hollow interior space between the wings 108 until it encounters a rearward-facing element 118, which may be a rounded cone or any suitable shape for dividing and spreading graft material injected from the posterior end 106 of the implant 100. The rearward-facing element 118 causes introduced graft material to spread in a predictable fashion to fully inundate an intervertebral region surrounding the implant 100 when the implant is inserted into a patient. The cavity 116 may also possess threads or other connecting features such notches, grooves, other positive or negative surface features, or other connecting features, for enabling rigid attachment of the implant 100 to an insertion device, so that a practitioner can readily manipulate the position of the implant 100 during insertion or during a revision procedure.

Figure 2:
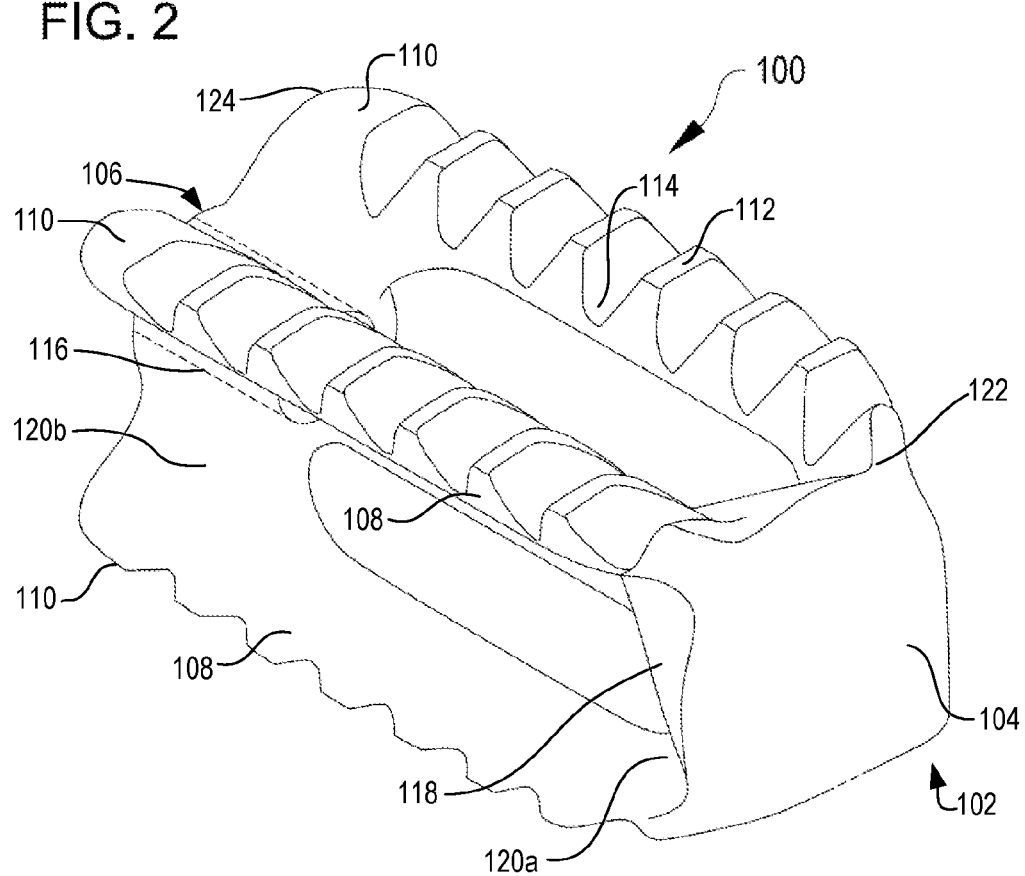

FIG. 2 is a perspective view of the intervertebral fusion implant 100 of FIG. 1 showing the substantially open construction of the implant 100, with a space between the wings 108 in both vertical and horizontal directions 132, 134.

Figure 3:
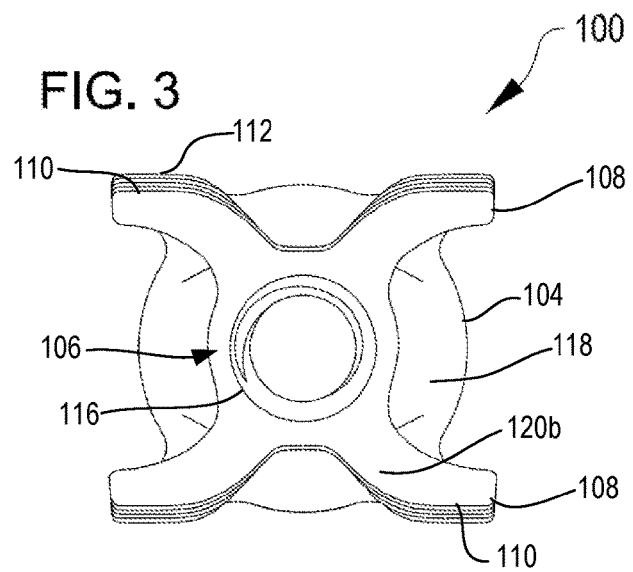

FIG. 3 is a posterior end view of the intervertebral fusion implant 100 of FIGS. 1 and 2. In the posterior end view, the size of the anterior cone 104 (and rearward-facing element 118) relative to the wings 108, posterior outer surface 110 and teeth 112 can be seen, with an outer diametrical edge of the cone 104 being approximately aligned with a plane intersecting the upper surface of the wings 108 at the anterior shoulders 122, and with a subset of the teeth 112 extending beyond this plane. Also shown is the cylindrical cavity 116, which may accommodate attachment to an insertion device, the insertion of graft material therethrough, or both.

Figure 4:
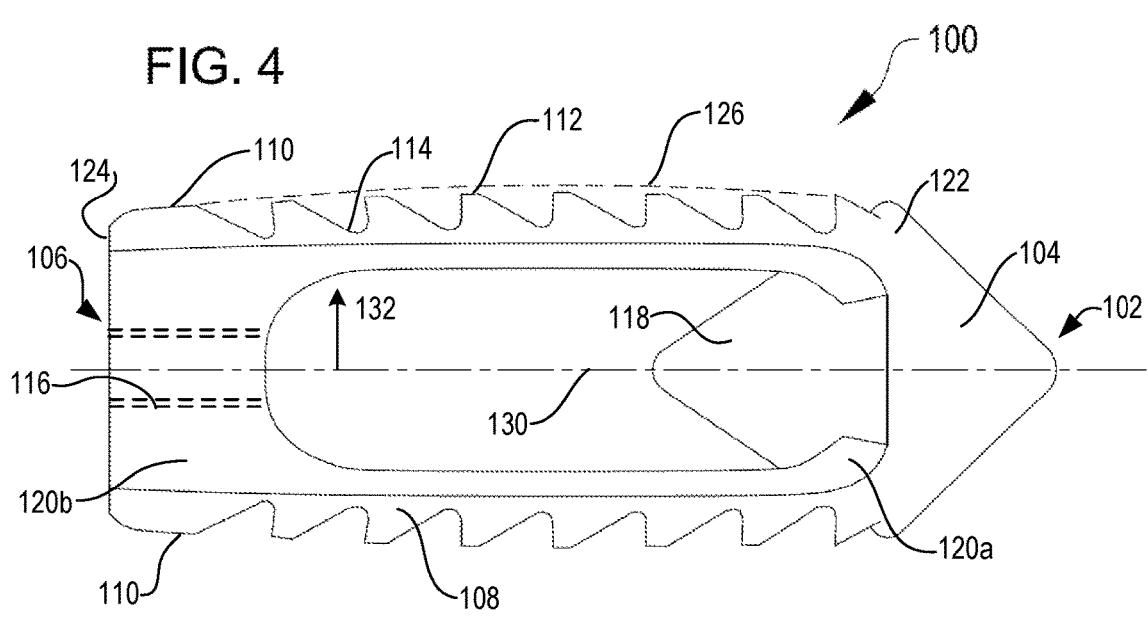

FIG. 4 is a side view of the intervertebral fusion implant 100 of FIGS. 1-3 illustrating the thickness of the wings 108 compared to their width (shown in FIG. 1). This thickness is tuned to provide the wings 108 with spring stiffness such that they can bend in response to a load. As described above, the upper edges of the teeth 112 define a shallow arc 126 that is convex in a direction away from the implant 100 as shown. The upper edges of the teeth 112 can also be convex about the central axis (see FIG. 5). The arc 126 can have a radius of curvature such that, when the wings 108 are loaded (e.g., when the implant 100 has been inserted between vertebrae), the wings 108 bend, increasing the radius of curvature of the arc 126. Under some loading conditions, the arc 126 can flatten such that the teeth 112 instead define a plane in a pre-loaded configuration.

Figure 5:
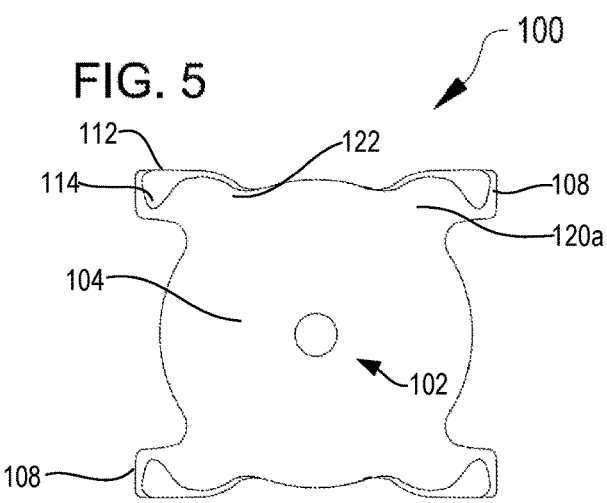

FIG. 5 is an anterior end view of the intervertebral fusion implant 100 of FIGS. 1-4 illustrating a first of multiple of the grooves 114 between teeth 112 of each wing 108, as well as the curved anterior shoulders 122. The anterior cone 104 may permit a physician to press the implant 100 into position between vertebrae using the cone 104 to increase the size (e.g., height, width, or both) of the opening into which the implant is received.

Figure 6:
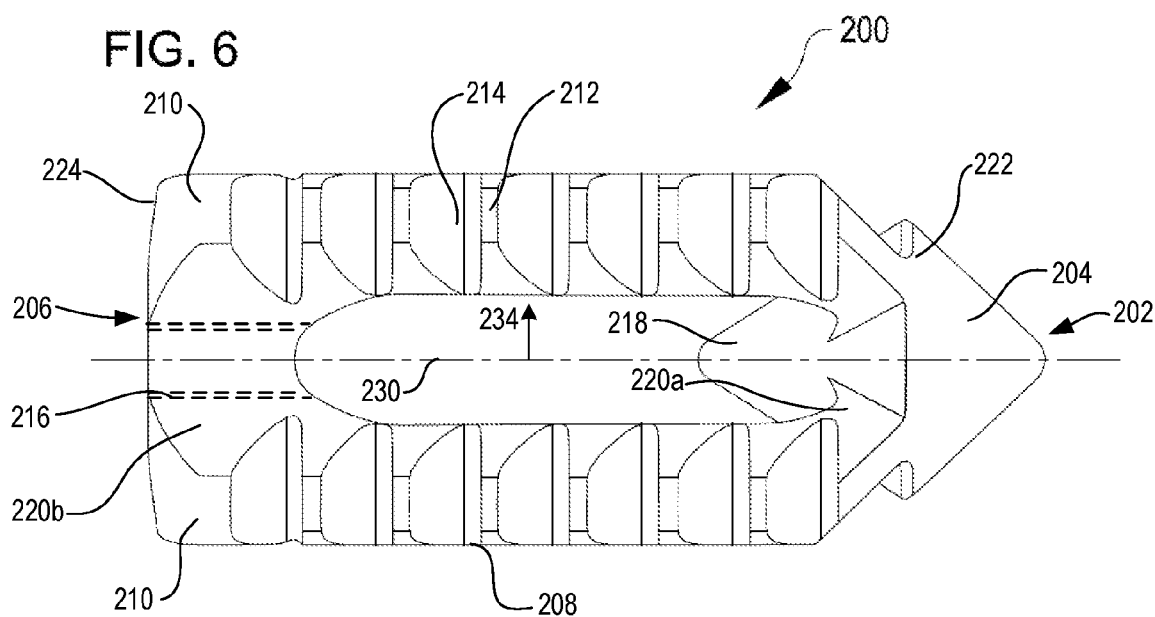
FIGS. 6-10 show a second example of an intervertebral fusion implant having a rounded conical anterior end element that is narrowed in comparison to the example shown in FIGS. 1-5, in various views, including: a top view (FIG. 6), a perspective view (FIG. 7), a posterior view (FIG. 8), a side view (FIG. 9) and an anterior view (FIG. 10)

The intervertebral implant may possess variations of the features disclosed above. For example, FIG. 6 shows a top view of a second intervertebral implant 200. The implant 200, like implant 100 in FIGS. 1-5, has an anterior end element 202. The tip of the anterior end element 202 defines a central axis 230 of the implant 200, and connects with an anterior cone 204 that increases in size (e.g., in horizontal and vertical directions 234, 232 (FIG. 6, FIG. 9)) from a minimum at the tip of the anterior end element 202 to a maximum at the curved anterior shoulders 222. The anterior cone 204 is connected with anterior structural members 220a that support four wings 208. The wings 208 join a posterior end 206 of the implant via posterior structural members 220b. Each of the wings 208 includes a wing outer surface 210 that has teeth 212 separated by grooves 214. The implant 200 further includes posterior shoulders 224 and a cylindrical cavity 216 in the posterior end 206.

Compared to the first implant 100, the implant 200 shown in FIG. 6 possesses a more pronounced curvature of the posterior shoulders 224 and a smaller maximum diameter of the anterior cone 204 (compared to posterior shoulder 124 and anterior cone 104). The reduction of material may decrease the effective stiffness of the implant by, for example, increasing the spring length of the anterior structural members 220a. As with the first implant 100, the wings 208, anterior end element 202, and posterior end 206 define a substantially open space therebetween along the central axis 230.

Figure 7:
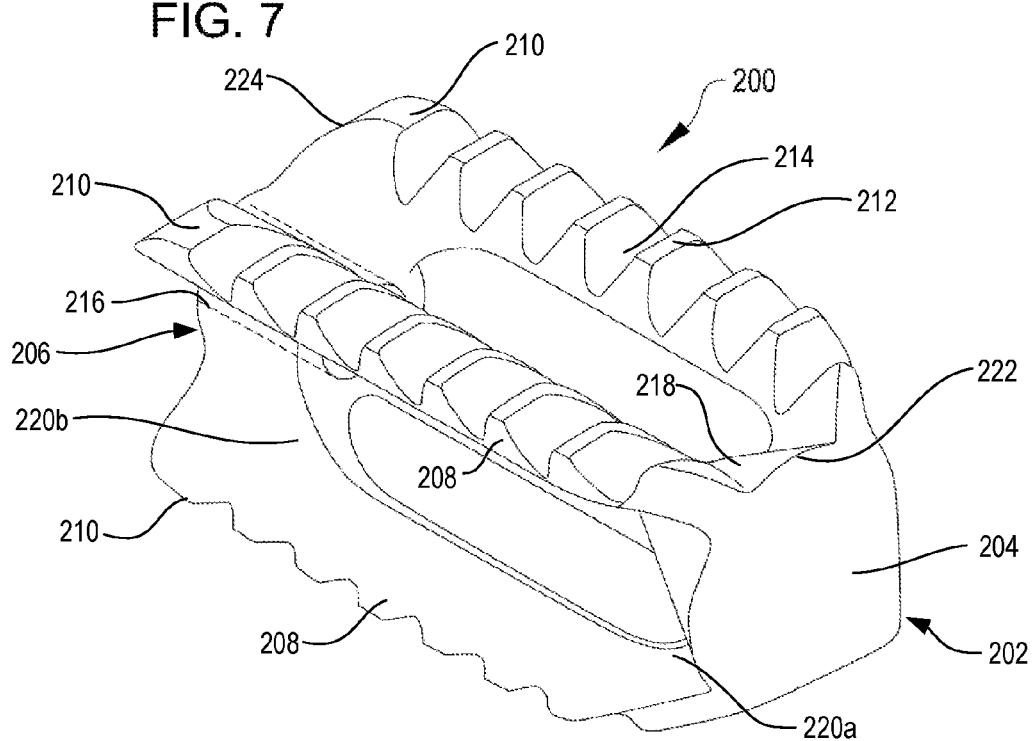

FIG. 7 is a perspective view of the intervertebral fusion implant 200 of FIG. 2 showing the substantially open construction of the implant 200, with a space between the wings 208 in both vertical and horizontal directions 232, 234.

Figure 8:
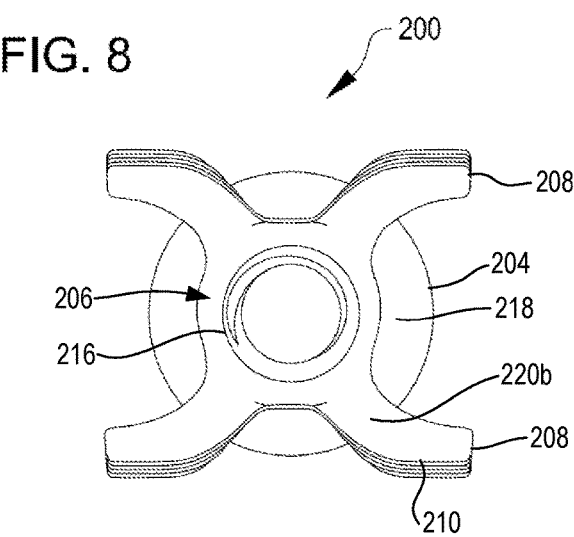

FIG. 8 is a posterior end view of the intervertebral fusion implant 200 of FIGS. 6 and 7 illustrating the smaller diameter of the anterior cone 204. Also shown is the coaxial alignment of the rearward-facing element 218 and the cylindrical cavity 216 in the posterior end 206 of the implant 200. As in the implant 100 of FIGS. 1-5, the cylindrical cavity 216 may provide for the attachment of an insertion device to the implant, the insertion of the graft material, or both. Likewise, as in the implant 100 of FIGS. 1-5, the rearward-facing element 218 may help to cause graft material introduced to the implant to flow and inundate the surgical site if funneled into the implant from a posterior direction.

Figure 9:
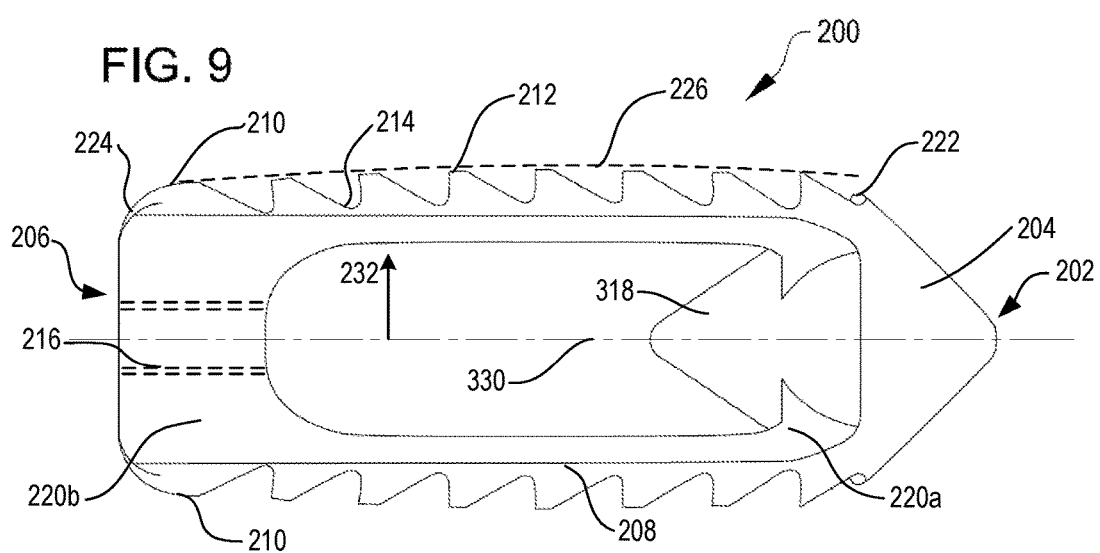

FIG. 9 is a side view of the intervertebral fusion implant 200 of FIGS. 6-8 showing a smaller anterior cone 204 (relative to the anterior cone 104 of the implant 100 shown in FIGS. 1-5). The maximum height of the anterior cone 204 (proximate to the anterior shoulders 222) in the vertical direction 232 aligns approximately with the grooves 214 between the teeth 212 on the wings 208. The peaks of the teeth 212 define a shallow arc 226 that is convex in a direction away from the implant 200. The arc 226 can have a radius of curvature such that, when the wings 208 are loaded (e.g., when the implant 200 has been inserted between vertebrae), the wings 208 can bend and the radius of curvature of the arc 226 increases. In some loading conditions, the arc 226 can flatten such that the peaks of the teeth 212 instead define a plane in a pre-loaded configuration.

Figure 10:
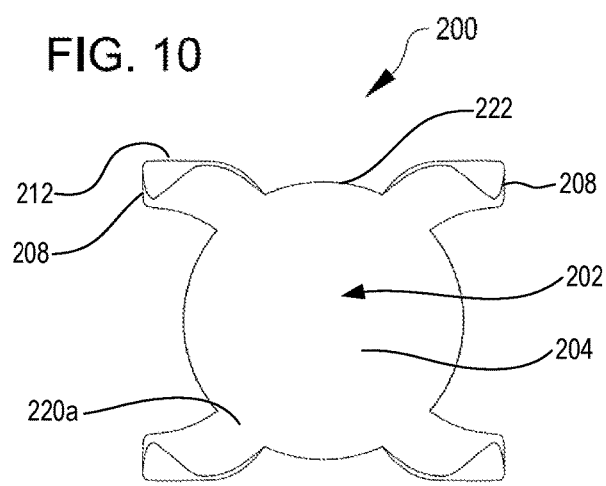

FIG. 10 is an anterior end view of the intervertebral fusion implant 200 of FIGS. 6-9 showing the increased length (i.e., cantilever length) of the anterior structural members 220a that support the wings 208 (relative to the anterior structural members 120a of the implant 100 shown in FIGS. 1-5). The narrower anterior cone 204 (compared to anterior cone 104 in FIGS. 1-5) may provide some mechanical widening of an insertion side when the implant 200 is received in a patient, while allowing the teeth 212 to engage the insertion site with minimal interference from the anterior cone 204.

Figure 11:
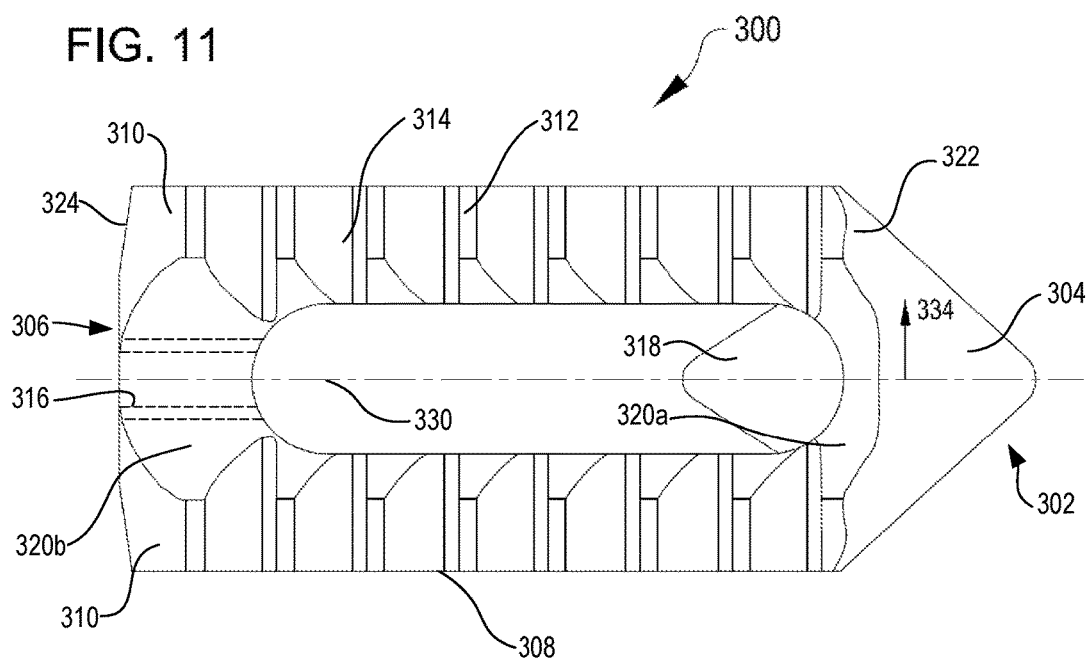
FIGS. 11-15 show a third example of an intervertebral fusion implant having a rounded pyramidal anterior end element in various views, including: a top view (FIG. 11), a perspective view (FIG. 12), a posterior view (FIG. 13), a side view (FIG. 14) and an anterior view (FIG. 15)

FIG. 11 shows a third intervertebral implant 300 having an anterior end element 302, a posterior end 306, and four wings 308 between them connected at the anterior and posterior ends by anterior and posterior structural members 320a, 320b, respectively. A pyramidal-shaped anterior wedge 304 with rounded edges increases in cross-sectional area from the tip of the anterior end element 302 until it terminates at anterior shoulders 322 that connect with the wings 308. Accordingly, a size of the square pyramidal-shaped anterior wedge 304 increases from a minimum size (e.g., in horizontal and vertical directions 334, 332 (FIG. 11, FIG. 14)) at the tip of the anterior end element 302 to a maximum size proximate to the anterior shoulders 322. At the posterior end of each of the wings 308, a posterior shoulder 324 curves from an outer surface 310 of the wings 308 to the posterior end 306 of the implant 300. The outer surface 310 of each of the wings 308 includes teeth 312 and grooves 314 with peaks running in a shallow arc 326 (see FIG. 14) between the anterior and posterior shoulders 322, 324. The implant 300 also includes a rearward-facing element 318 within a space between the wings 308 and a cylindrical cavity 316 in the posterior end 306 of the implant. The rearward-facing element 318 decreases in cross sectional area from a maximum cross-sectional area proximate to the anterior shoulders 322 to a minimum cross-sectional area in an open space between the wings 308, in the direction of the posterior end 306 of the implant 300. The rearward-facing element 318 may help to cause graft material introduced to the implant to flow and inundate the surgical site if funneled into the implant from a posterior direction. As with the first implant 100, the wings 308, the anterior end element 302, and the posterior end 306 define a substantially open space therebetween along the central axis 330.

Figure 12:
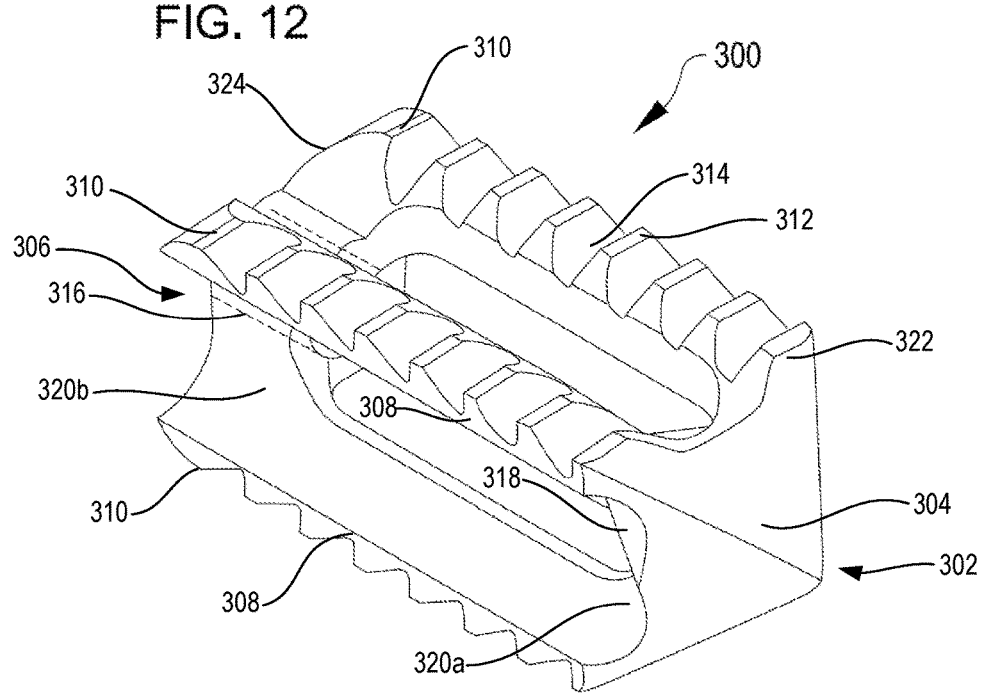

FIG. 12 is a perspective view of the intervertebral fusion implant 300 of FIG. 11 showing the open interior space between the wings 308.

Figure 13:
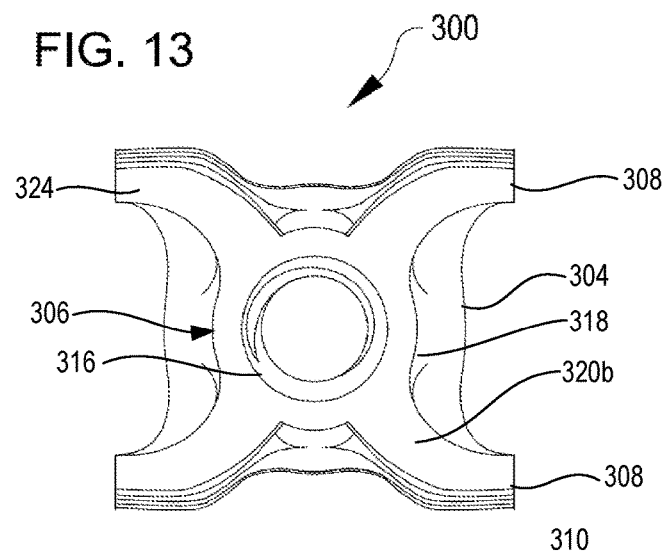

FIG. 13 is a posterior end view of the intervertebral fusion implant 300 of FIGS. 11 and 12 showing the cylindrical cavity 316 in the posterior end 306 of the implant 300. Also shown are posterior structural members 320b that are configured to act as cantilevered spring members and that originate from the posterior end 306 of the implant 300.

Figure 14:
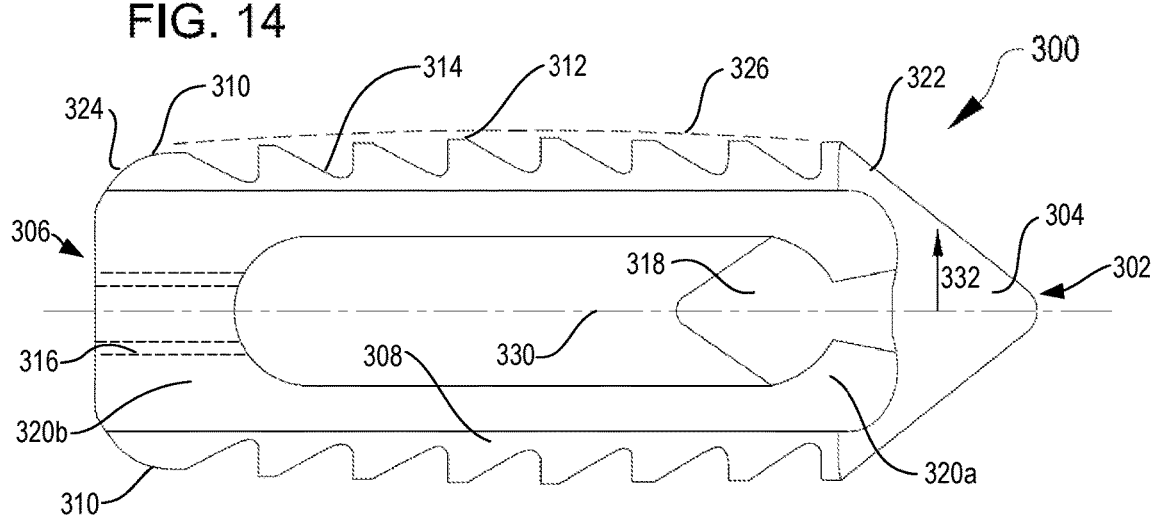

FIG. 14 is a side view of the intervertebral fusion implant 300 of FIGS. 11-13 showing the open space between the wings 308, as well as the shallow arc 326 defined by peaks of the teeth 312 on the wings 308. The arc 326 is convex in a direction away from the implant 300. The arc 326 can have a radius of curvature such that, when the wings 308 are loaded (i.e., when the implant 300 has been inserted between vertebrae), the wings 308 can bend and the radius of curvature of the arc 326 increases. In some loading conditions, the arc 326 can flatten in response to a load such that the peaks of the teeth 312 instead define a plane. In some cases, the arc 326 may be flattened into a planar, pre-loaded configuration and retained in the pre-loaded configuration. The implant 300 may be allowed to expand into an expanded configuration after insertion into an intervertebral space.

Figure 15:
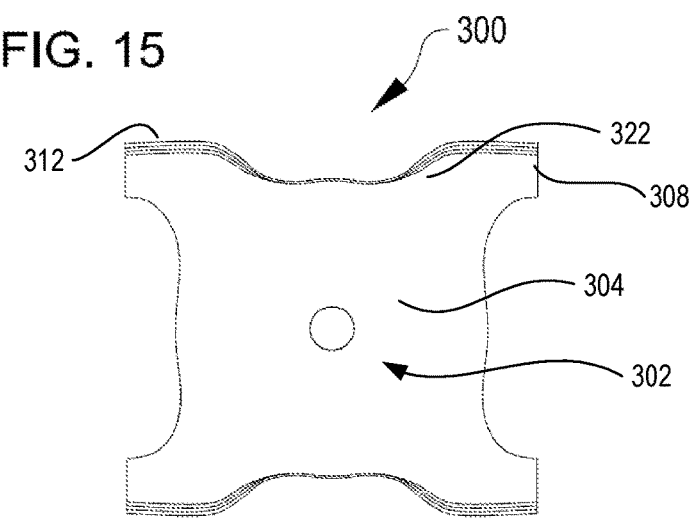

FIG. 15 is an anterior end view of the intervertebral fusion implant 300 of FIGS. 11-14 illustrating the square pyramidal shape of the anterior wedge 304, which may provide a mechanical advantage during insertion of the implant 300 (similar to the anterior cones 104, 204 of implants 100 and 200) while also providing for axial alignment of the implant 300 with the vertebrae of a patient.

Figure 16:
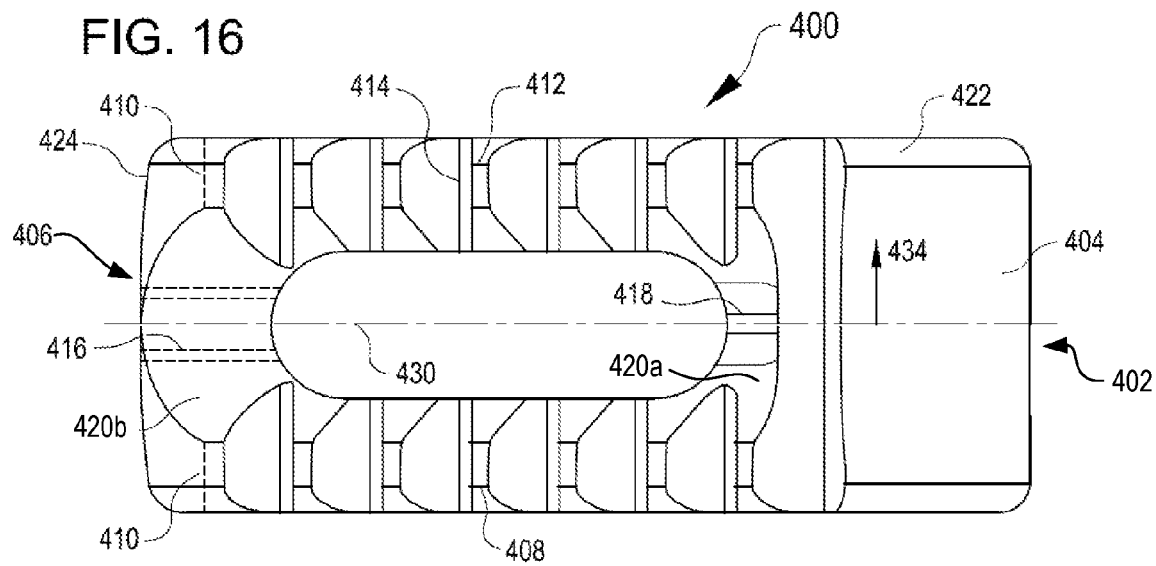
FIGS. 16-20 show a fourth example of an intervertebral fusion implant having a rounded wedge-shaped anterior end element in various views, including: a top view (FIG. 16), a perspective view (FIG. 17), a posterior view (FIG. 18), a side view (FIG. 19) and an anterior view (FIG. 20)

FIG. 16 shows a fourth intervertebral implant 400 having an anterior end element 402, a posterior end 406, and four wings 408 disposed between them. The anterior end element 402 includes a rounded peak of a flat wedge 404 having a rectangular cross-section with rounded corners. The flat wedge 404 has substantially the same cross section along a horizontal direction 434, but widens in the vertical direction 432 (FIG. 19) from the tip of the anterior end element 402 toward the posterior end 406 (see, e.g., FIG. 19). The flat wedge 404 includes anterior shoulders 422 at an outer edge of the flat wedge 404. The implant 400 also has posterior shoulders 424 which curve from the outer surfaces 410 of the wings 408 and join with the posterior end 406 of the implant 400. The implant 400 also has a cylindrical cavity 416 (see FIG. 18) in the posterior end 406 and a rearward-facing surface feature 418 (see FIG. 19) disposed behind the wedge 404 and facing the posterior end 406. As with the first implant 100, the wings 408, anterior end element 402, and posterior end 406 define a substantially open space therebetween along the central axis 430.

Figure 17:
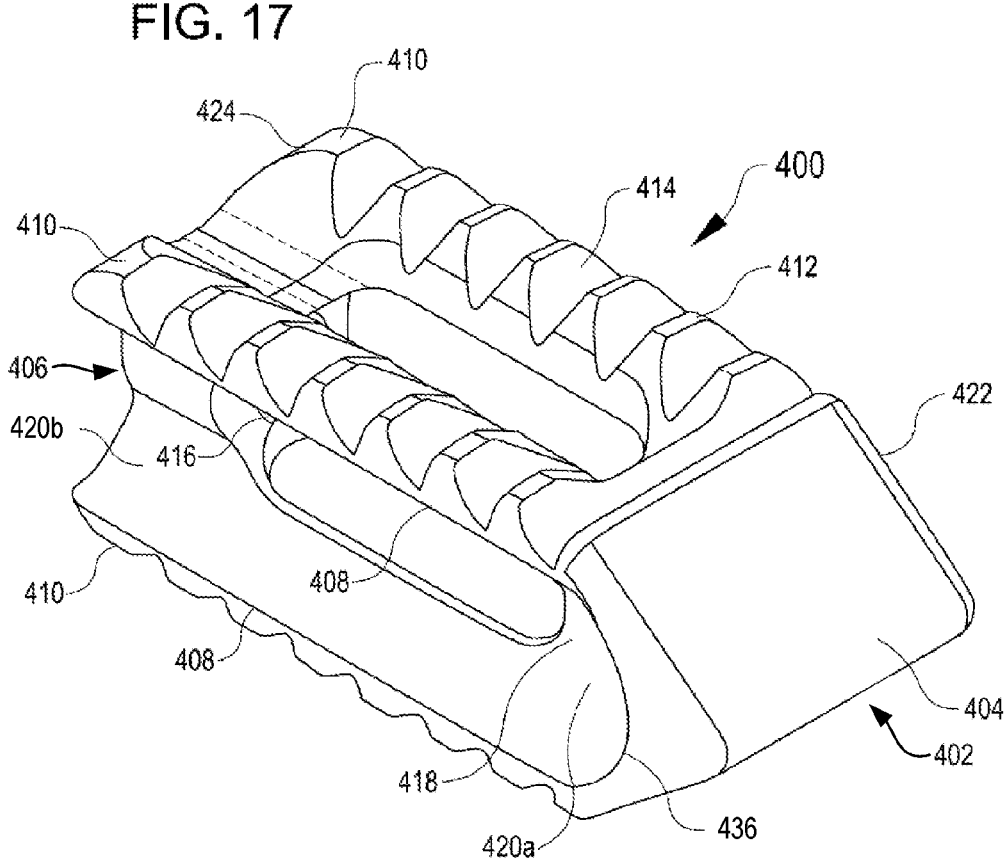

FIG. 17 is a perspective view of the intervertebral fusion implant 400 of FIG. 16 showing the open interior space between the wings 408. Each of the sides of the wedge 404 define a curved void 436, which merges with anterior structural members 420a that connect the wings 408 to each other adjacent to the anterior wedge 404. The wings 408 merge with posterior structural members 420b that connect the wings with the posterior end 406 of the implant 400.

Figure 18:
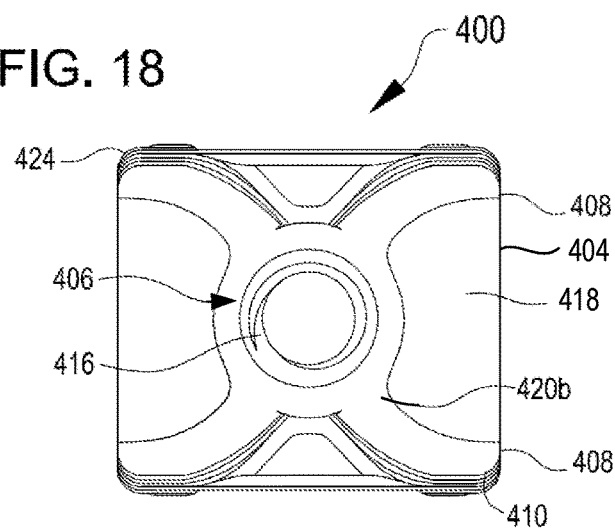

FIG. 18 is a posterior end view of the intervertebral fusion implant 400 of FIGS. 16 and 17 illustrating the cylindrical cavity 416 in the posterior end 406 of the implant. This cavity 416 may be configured for attachment with an insertion device, for example by having threads or other connecting features, or may be configured to accommodate injecting a graft material therethrough, or both.

Figure 19:
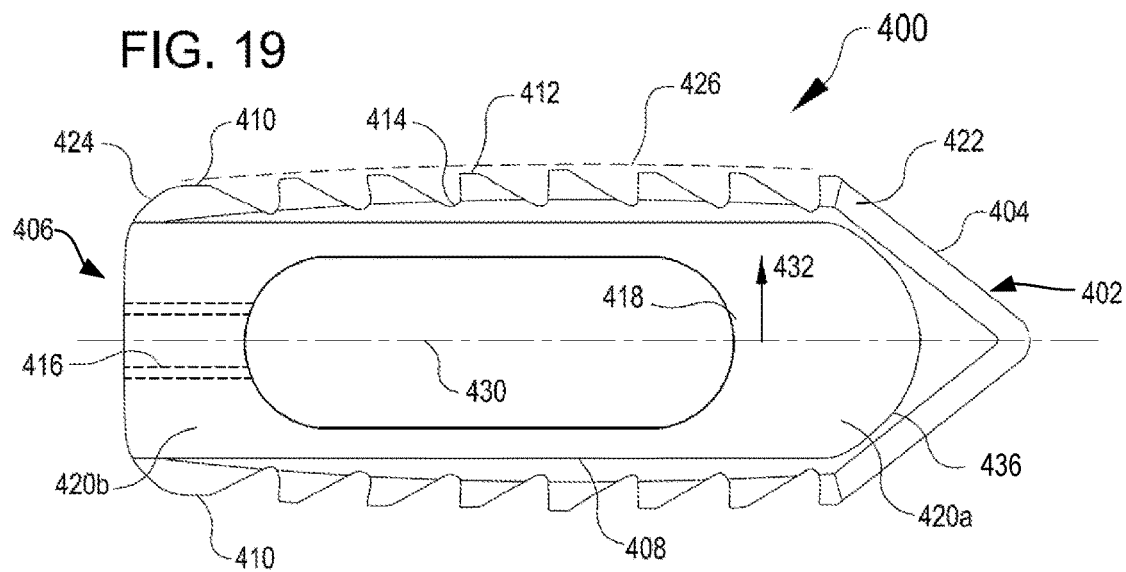

FIG. 19 is a side view of the intervertebral fusion implant 400 of FIGS. 16-18 illustrating the widening (in the vertical direction 432) anterior wedge 404, the open space between the wings 408, as well as a shallow arc 426 defined by the peaks of the teeth 412 on the outer surface 410 of the wings 408, and the rearward-facing feature 418. A height of the anterior wedge 404 increases from a minimum to a maximum in the vertical direction 432 from the tip of the anterior end element 402 of the implant 400 to the anterior shoulders 422, respectively. The rearward-facing feature 418 may be any suitable shape for dividing and spreading graft material injected from the posterior end 406 of the implant 400. The arc 426 is convex in a direction away from the implant 400. The arc 426 can have a radius of curvature such that, when the wings 408 are loaded (i.e., when the implant 400 has been inserted between vertebrae), the wings 408 can bend and the radius of curvature of the arc 426 increases. In some loading conditions, the arc 426 can flatten under a load such that the peaks of the teeth 412 instead define a plane. In some cases, the arc 426 may be flattened into a planar, pre-loaded configuration and retained in the pre-loaded configuration. The implant 400 may be allowed to expand into an expanded configuration after insertion into an intervertebral space.

Figure 20:
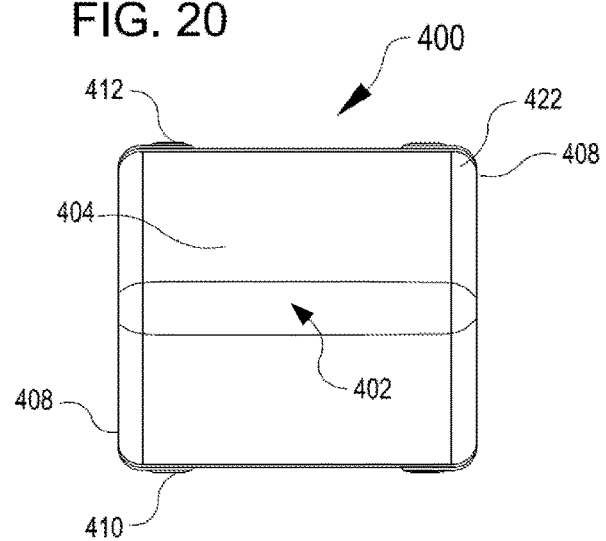

FIG. 20 is an anterior end view of the intervertebral fusion implant 400 of FIGS. 16-19 showing the anterior wedge 404, which may be suitable for aligning the implant 400 with a space between vertebrae, such that a pressing operation will cause the wedge to expand the space between said vertebrae in order to receive the implant 400.

Figure 21:
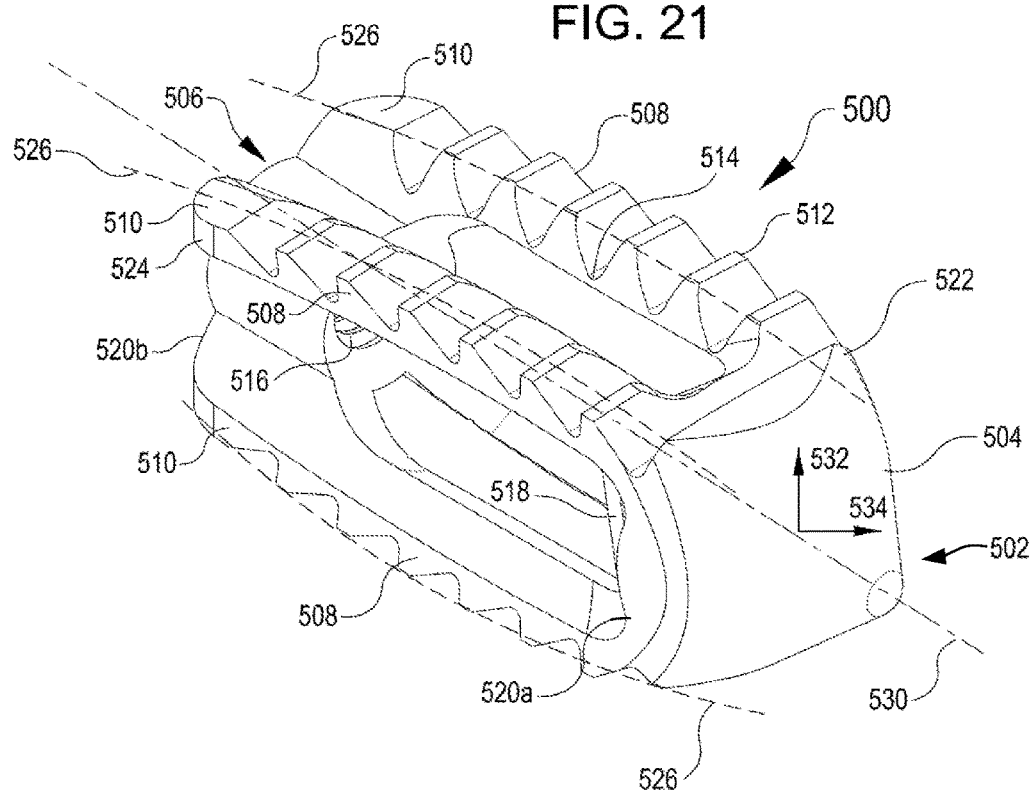
FIGS. 21-24 show a fifth example of an intervertebral fusion implant having a rounded conical anterior end element in various views, including: a perspective view (FIG. 21), a posterior view (FIG. 22), a top view (FIG. 23), and a side view (FIG. 24)

FIG. 21 shows a fifth intervertebral implant 500 in a perspective view. The implant 500 has an anterior end element 502 in the form of a rounded anterior cone 504 configured for facilitating insertion of the implant in a patient in a PLIF procedure. The anterior end element 502 is positioned opposite a posterior end 506. A central axis 530 runs through the implant 500, orthogonal to a vertical direction 532 and a horizontal direction 534. The anterior cone 504 terminates at anterior shoulders 522. Four wings 508 aligned with the anterior shoulders 522 join the anterior end element 502 and the posterior end 506 via anterior and posterior structural members 520a, 520b, respectively. The wings 508 originate at the anterior structural members 520a and terminate with a curved shoulder 524 at each of the posterior structural members 520b. The top pair of wings 508 have outer surfaces 510 pointing upward and the bottom pair of wings 508 have outer surfaces pointing downward in the vertical direction 532. The outer surfaces 510 have alternating teeth 512 and grooves 514. The teeth 512 follow a curvature of an arc 526 that is convex away from the implant 500. The posterior end 506 of the implant 500 has a cylindrical cavity 516 therethrough. The cylindrical cavity 516 can include attaching features for an installation tool, such as but not limited to, threads (as shown), notches, grooves, other positive or negative surface features, or other connecting features. Opposite the anterior cone 504 at the anterior end element 502 of the implant 500, a rearward-facing element 518 faces toward the cylindrical cavity 516. The rearward-facing element 518 may be any suitable shape for dividing and spreading graft material injected from the posterior end 506 of the implant 500, from a transverse direction, or both. As with the first implant 100, the wings 508, the anterior end element 502, and posterior end 506 define a substantially open space therebetween along the central axis 530.

Figure 22:
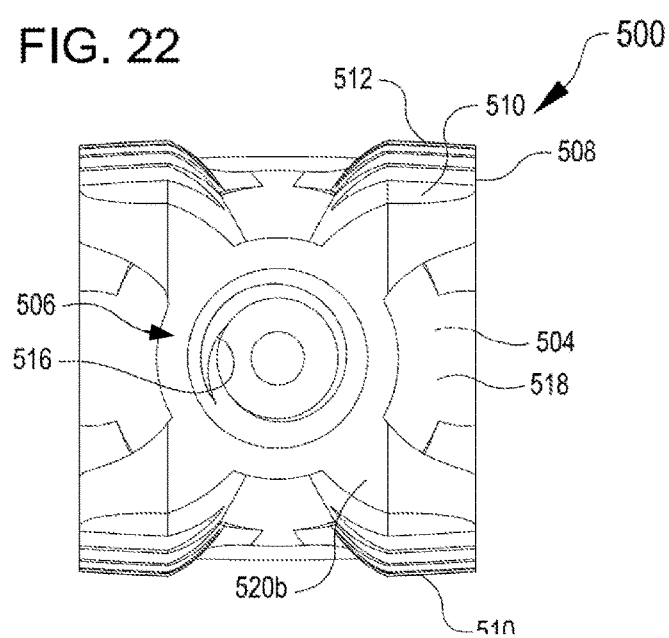

FIG. 22 shows the intervertebral implant 500 of FIG. 21 in a posterior view. In the posterior view, the positioning of the rearward-facing element 518 with respect to the cylindrical cavity 516 can be seen more clearly. The projection of the teeth 512 outward from the implant 500 beyond the wing faces 510 is also visible.

Figure 23:
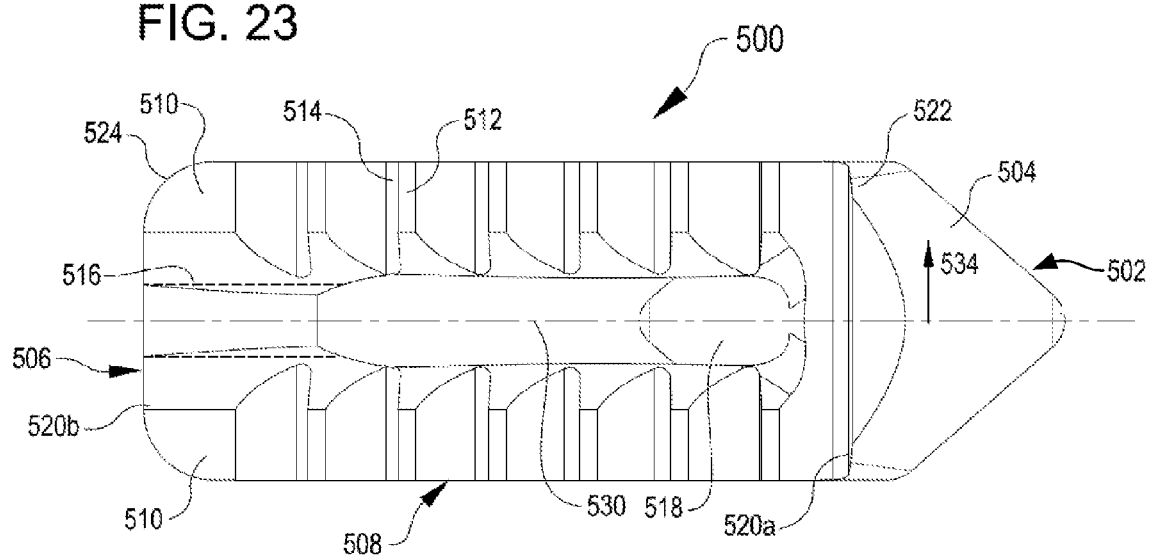

FIG. 23 shows the intervertebral implant 500 of FIGS. 21-22 in a top view. The top view shows in greater detail the horizontal separation of the wings 508. As shown in FIG. 23, the width of the anterior cone 504 increases in the horizontal direction 534 from an anterior to posterior direction.

Figure 24:
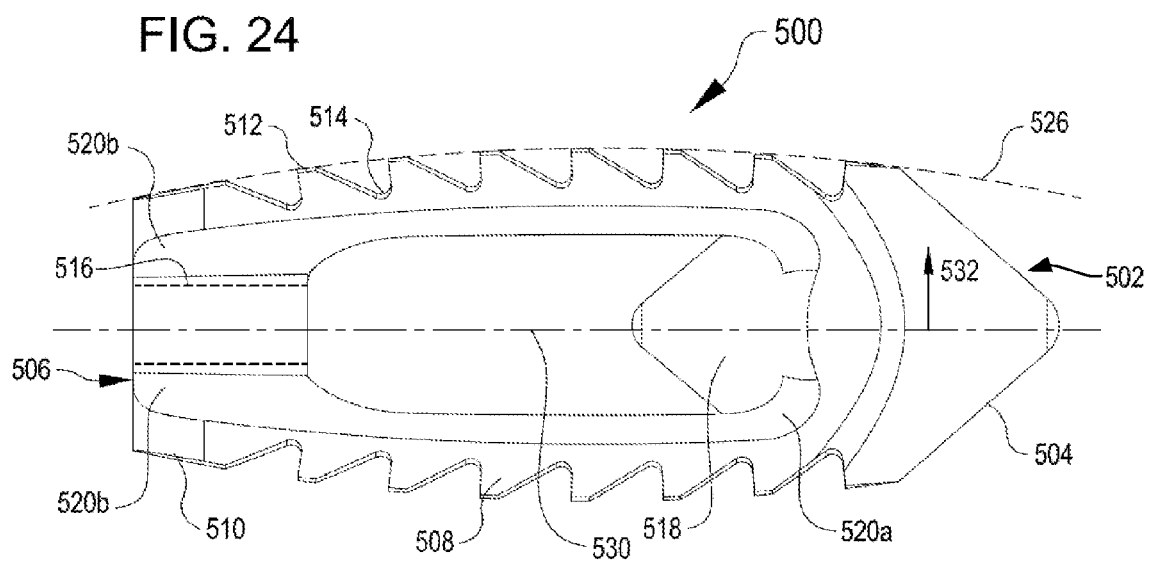

FIG. 24 shows the intervertebral implant 500 of FIGS. 21-23 in a side view. The side view more clearly illustrates the vertical separation of the wings 508, and the curvature of the arc 526 defined by the teeth 512 of the implant 500. As shown in FIG. 24, the height of the anterior cone 504 increases in the vertical direction 532 from an anterior to posterior direction. As described above, in some cases, the wings 508 can flex under load, such that the curvature of the arc 526 can at least partially flatten. Flexible wings 508 may permit the implant 500 to engage more fully with the bone in an intervertebral space when the implant is installed in a patient.

Figure 25:
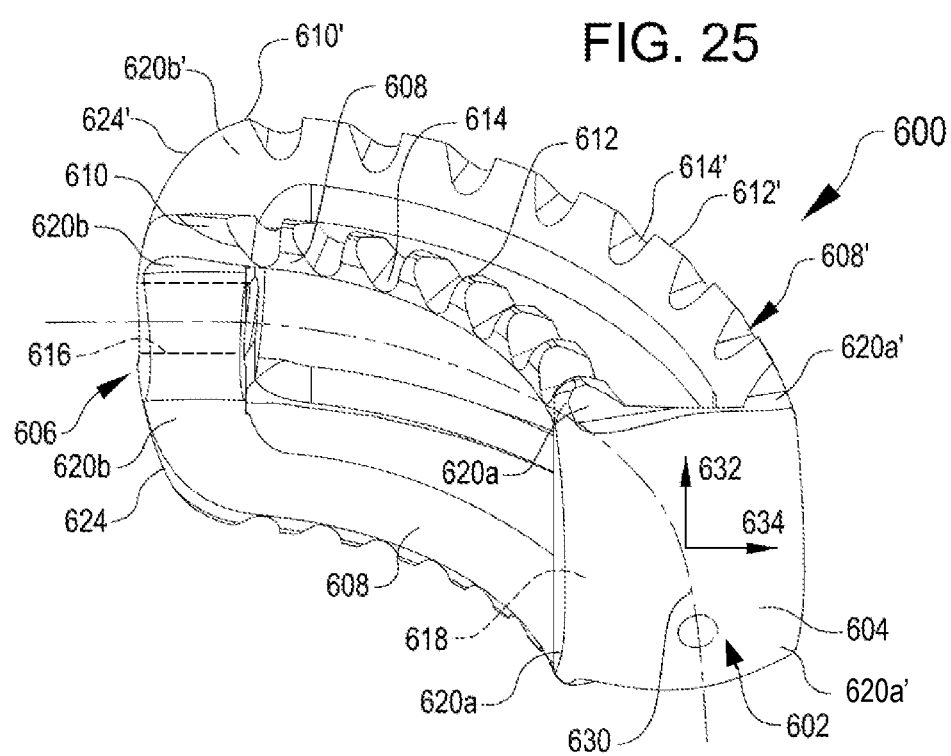
FIGS. 25-28 show a sixth example of an intervertebral fusion implant having a body curvature and a rounded anterior end element in various views, including: a perspective view (FIG. 25), a top view (FIG. 26), a side view (FIG. 27), and a posterior view (FIG. 28)

FIG. 25 shows a sixth intervertebral implant 600 in a perspective top view. The implant 600 differs from the previously described implants by having a lateral curvature configured for facilitating insertion of the implant in a patient in a TLIF procedure. The implant 600 is therefore asymmetrical in the horizontal direction 634. Accordingly, asymmetric aspects of the implant 600 are denoted separately below. The implant 600 has a rounded conical anterior end element 602 and a rounded anterior cone 604. The curved shape of the implant 600 is defined by a central curve 630 that runs through the implant 600 much like the central longitudinal axes of above-described implants. The central curve 630 can be defined as a partial circular section, or may be defined as an irregular curve or spline shape to accommodate a curvature of an interstitial space between vertebrae. Aspects of the implant 600 may be described with reference to a vertical direction 632 and horizontal direction 634 orthogonal relative to the central curve 630.

Wings 608, 608' (wherein 608 denotes the two inner wings and 608' denote the two outer wings along the horizontal direction 634) join the anterior end element 602 and the posterior end 606 via anterior and posterior structural members 620a, 620a', and 620b, 620b' respectively (wherein 620a, 620b denote inner structural members and 620a', 620b' denote outer structural members). The wings 608, 608' originate at the anterior structural members 620a, 620a' and terminate with curved posterior shoulders 624, 624' (wherein 624 denotes inner curved shoulders and 624' denotes outer curved shoulders) at the posterior structural members 620b, 620b'. The outer wings 608' are longer than the inner wings 608, as illustrated. The upper wings 608, 608' have an outer surface 610, 610', respectively, that points upward in the vertical direction 632 while the lower wings 608, 608' have an outer surface 610, 610', respectively, that points downward in the vertical direction 632. The outer surfaces 610, 610' have alternating teeth 612, 612' and grooves 614, 614'. The posterior end 606 of the implant 600 has a cylindrical cavity 616 therethrough. The cylindrical cavity 616 can include attaching features for an installation tool, such as but not limited to, threads (as shown), notches, grooves, or other positive or negative surface features. Opposite the anterior cone 604 at the anterior end element 602 of the implant 600, a blunt rearward-facing surface 618 faces toward the cylindrical cavity 616. The rearward-facing surface feature 618 helps spread graft material injected from the posterior end 606 of the implant 600. As with the first implant 100, the wings 608, 608', the anterior end element 602, and the posterior end 606 define a substantially open space therebetween along the central curve 630.

Figure 26:
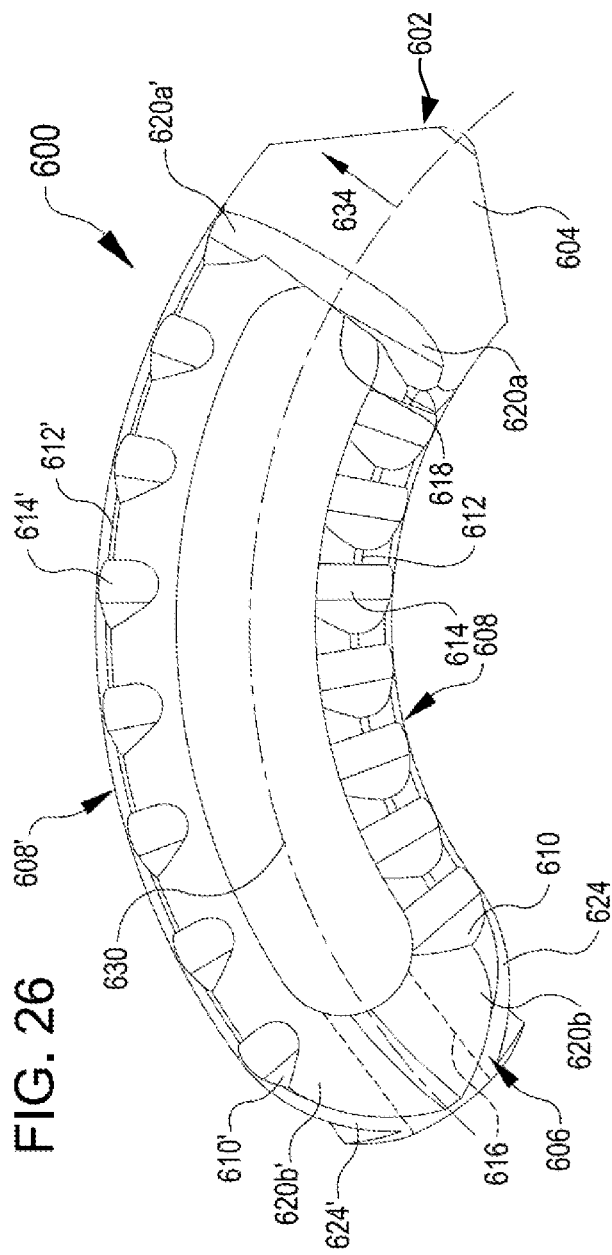

FIG. 26 shows the intervertebral implant 600 of FIG. 25 in a top view. In the top view, the curve of the implant 600 along the central curve 630 is more clearly visible. In the implant 600 as shown, the number of teeth 612, 612' on each wing 608, 608' is the same, and the matching pairs of grooves 614, 614' are approximately or identically the same size, although they need not be. For example, fewer teeth 612 may be present on the inner wings 608 compared to the number of teeth 612' on the outer wings 608'. The top view also shows the implant 600 curving in a first direction, although the implant could be curved in the opposite direction. Furthermore, the implant 600 as shown is symmetrical about a horizontal plane on which the central curve 630 is defined, such that the direction of the curve of the implant can be reversed by inverting the implant. However, in some alternatives, curved implants may be asymmetrical.

Figure 27:
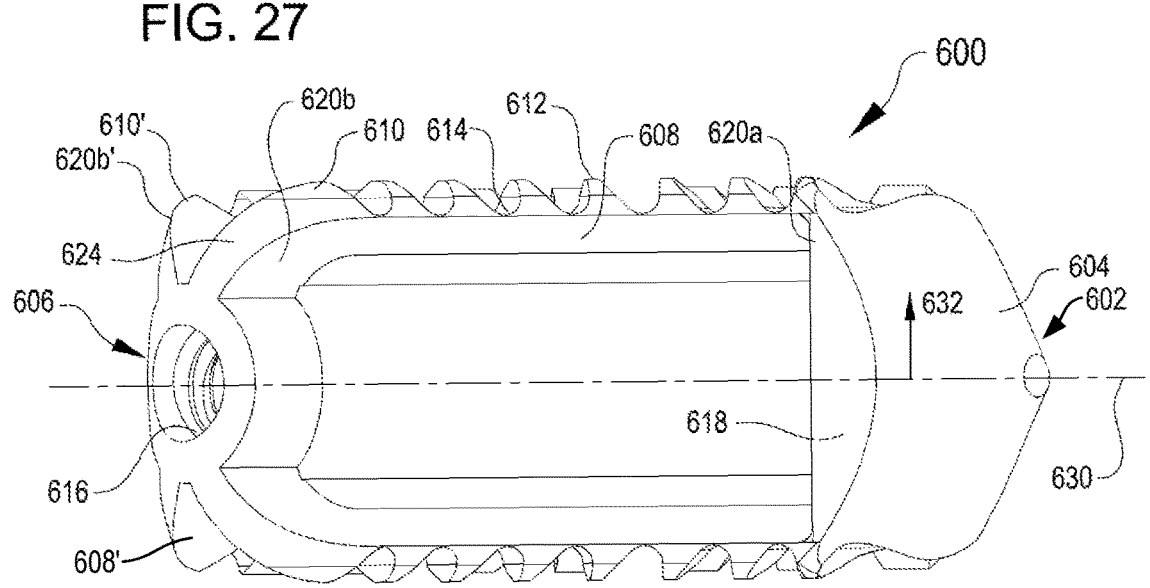

FIG. 27 shows the intervertebral implant 600 of FIGS. 25-26 in a side view. In the side view, the vertical symmetry of the implant 600 is more clearly visible.

Figure 28:
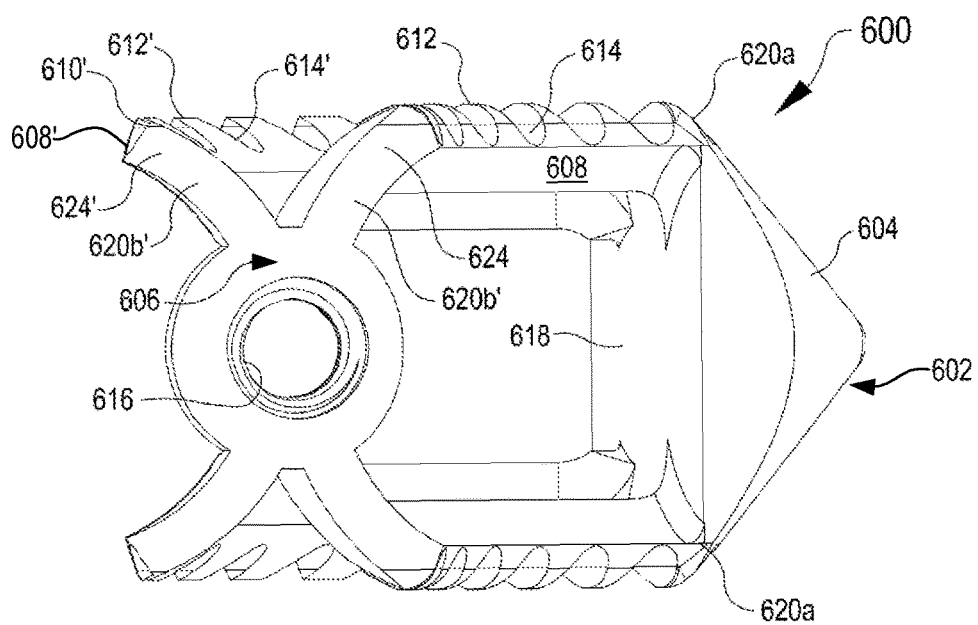

FIG. 28 shows the intervertebral implant 600 of FIGS. 25-27 in a posterior view. In the posterior view, the positioning of the cylindrical cavity 616 is more clearly visible in the posterior end 606 of the implant 600. The blunt rearward-facing surface 618 of the anterior end element 602 is also more clearly visible. In other examples, the blunt rearward-facing surface 618 may be replaced with a rearward-facing element such as a cone or other shaped structure, as previously described.

Figure 29:
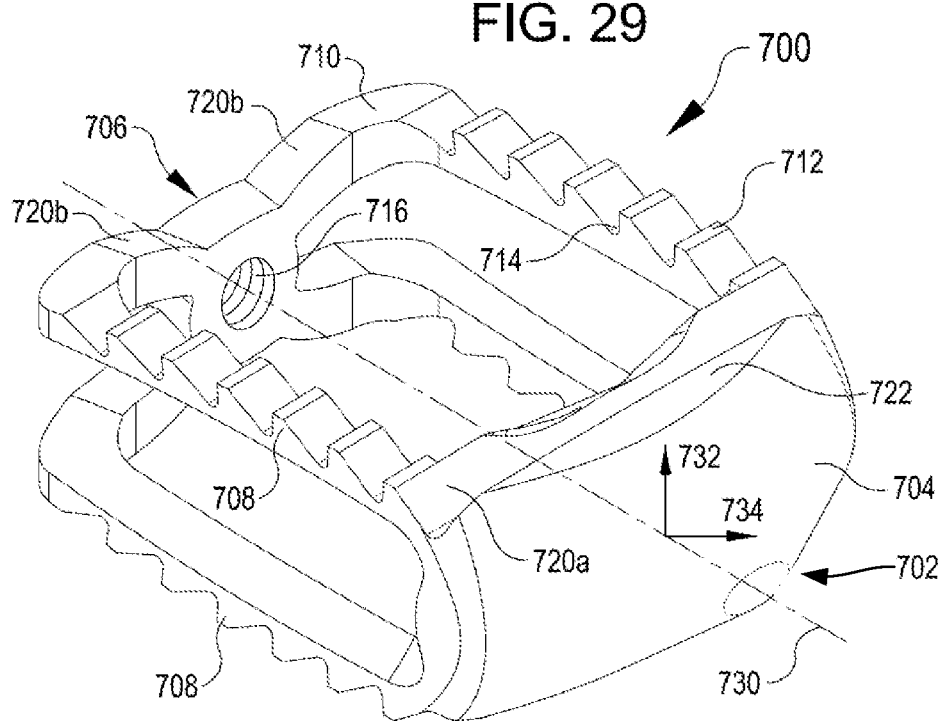
FIGS. 29-32 show a seventh example of an intervertebral fusion implant having a wide aspect ratio and a rounded anterior end element in various views, including: a perspective view (FIG. 29), a posterior view (FIG. 30), a top view (FIG. 31), and a side view (FIG. 32)

FIG. 29 shows a seventh intervertebral implant 700 in a perspective view. The implant 700 has an anterior end element 702 comprising a rounded anterior cone 704, and has a wide-bodied aspect ratio, configured for facilitating insertion of the implant 700 in a patient in a LLIF procedure. The anterior end element 702 is positioned opposite a posterior end 706. A central axis 730 runs through the implant 700, orthogonal to a vertical direction 732 and horizontal direction 734. The implant 700 is significantly wider in the horizontal direction 734 than in the vertical direction 732 to aid in supporting the significantly weight-bearing lumbar spine, and to provide ample space for inserting a high volume of graft material. The anterior cone 704 terminates at anterior shoulders 722.

Four wings 708 join the anterior end element 702 and the posterior end 706 via anterior and posterior structural members 720a, 720b. The anterior structural members 720a are posterior of the anterior shoulders 722. The wings 708 originate at the anterior structural members 720a and terminate with curved shoulders 724 (see FIG. 30) at the posterior structural members 720b. Each of the two top wings 708 has an outer surface 710 pointing upward in the vertical direction 732 and each of the two bottom wings 708 has an outer surface 710 pointing downward in the vertical direction 732. Each of the wing outer surfaces 710 has alternating teeth 712 and grooves 714. The wings 708 can be curved in the vertical direction 732, e.g., convex with respect to a horizontal plane passing through the central axis 730 of the implant 700. In some cases, the wings 708 may converge gradually from the anterior structural members 720a to the posterior structural members 720b. As with the first implant 100, the wings 708, the anterior end element 702, and the posterior end 706 define a substantially open space therebetween along the central axis 730.

The posterior end 706 of the implant 700 has a cylindrical cavity 716 therethrough. The cylindrical cavity 716 can include attaching features for an installation tool, such as but not limited to, threads (as shown), notches, grooves, or other positive or negative surface features. Opposite the anterior cone 704 at the anterior end element 702 of the implant 700, a rearward-facing element 718 faces toward the cylindrical cavity 716 (FIGS. 30-32).

Figure 30:
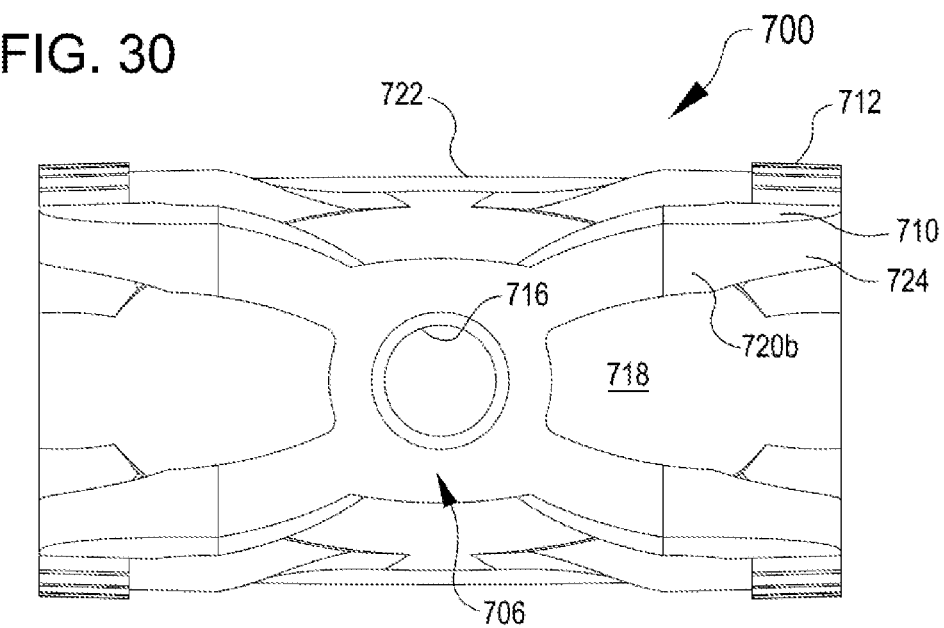

FIG. 30 shows the intervertebral implant 700 of FIG. 29 in a posterior view. The posterior view shows more clearly the wider aspect ratio of the implant 700, and the positioning of the cylindrical cavity 716 in the posterior end 706.

Figure 31:
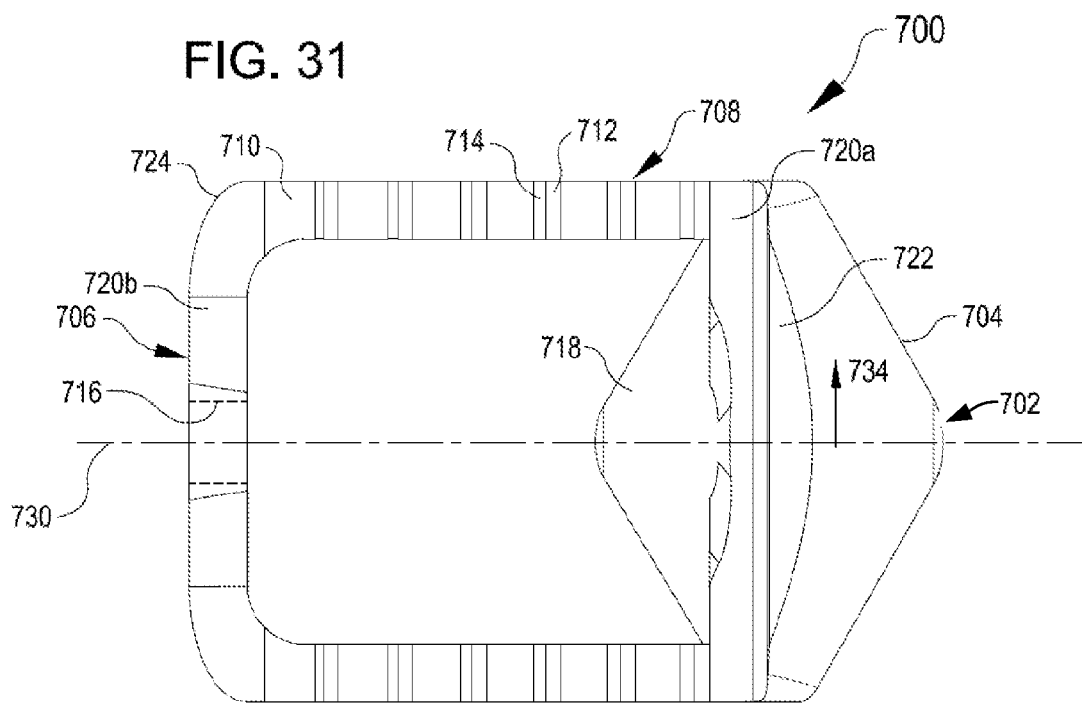

FIG. 31 shows the intervertebral implant 700 of FIGS. 29-30 in a top view. The top view shows more clearly the extension of the rearward-facing element 718 on a posterior side of the anterior end element 702, pointing toward the cylindrical cavity 716. The rearward-facing element 718 is configured to spread graft material when graft material is injected into the implant from the posterior end 706, e.g., through the cylindrical cavity 716.

Figure 32:
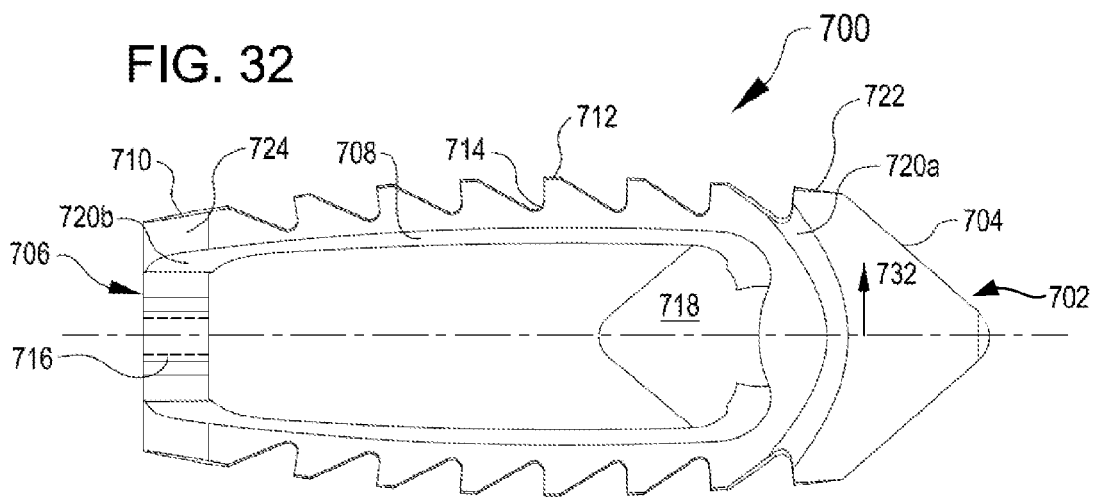

FIG. 32 shows the intervertebral implant 700 of FIGS. 29-31 in a side view. The side view shows more clearly the slope of the rearward-facing element 718, which is steeper in the vertical direction 732 than in the horizontal direction 734 (FIG. 31). Also shown more clearly is the gradual convergence of the wings 708 in the vertical direction 732 toward the central axis 730 from the anterior end element 702 to the posterior end 706.

Figure 33:
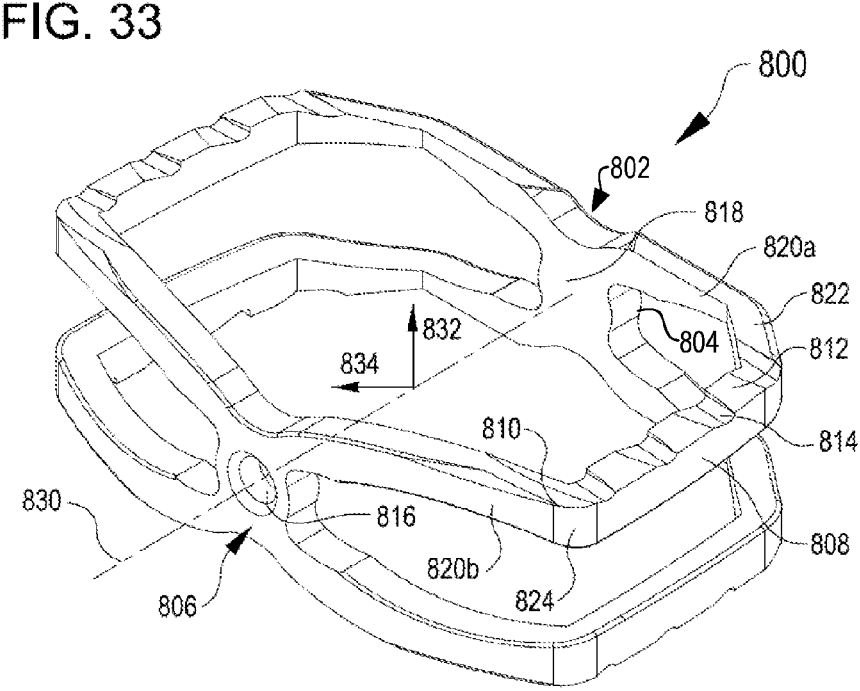
FIGS. 33-36 show an eighth example of an intervertebral fusion implant having a wide aspect ratio, including: a perspective view (FIG. 33), a top view (FIG. 34), a side view (FIG. 35), and a posterior view (FIG. 36)

FIG. 33 shows an eighth intervertebral implant 800 in a perspective view. The implant 800 has an anterior end element 802 comprising a blunt anterior surface 804 and a minimalist construction configured for facilitating insertion of the implant in a patient in an ALIF procedure and for accommodating a high volume of graft material. The reduction of material may decrease the effective stiffness of the implant by, for example, increasing the spring length of anterior and posterior structural members 820a, 820b. The anterior end element 802 is positioned opposite a posterior end 806. A central axis 830 runs through the implant 800, orthogonal to a vertical direction 832 and horizontal direction 834. As with the first implant 100, the wings 808, the anterior end element 802, and the posterior end 806 define a substantially open space therebetween along the central axis 830. The anterior surface 804 connects with sloped anterior shoulders 822 configured for facilitating ease of installation of the implant 800 in an intervertebral space.

Four wings 808 join the anterior end element 802 and the posterior end 806 via anterior and posterior structural members 820a, 820b. The wings 808 originate at the anterior structural members 820a and terminate with a posterior curved shoulder 824 at the posterior structural members 820b. Each of the two top wings 808 has an outer surface 810 pointing upward in the vertical direction 832 and each of the two bottom wings 808 has an outer surface 810 pointing downward in the vertical direction 832. Each outer surface 810 has alternating teeth 812 and grooves 814. The wings 808 can expand outward in the horizontal direction 834 away from the central axis 830 from the anterior end element 802 to the posterior end 806. The posterior curved shoulder 824 can define a curve to the posterior end 806 of the implant 800 for supporting a shape of an anterior portion of an intervertebral space.

The posterior end 806 of the implant 800 has a cylindrical cavity 816 therethrough. The cylindrical cavity 816 can include attaching features for an installation tool, such as but not limited to, threads (as shown), notches, grooves, or other positive or negative surface features. Opposite the blunt anterior surface 804 at the anterior end element 802 of the implant 800, a rearward-facing inner surface 818 faces toward the cylindrical cavity 816.

Figure 34:
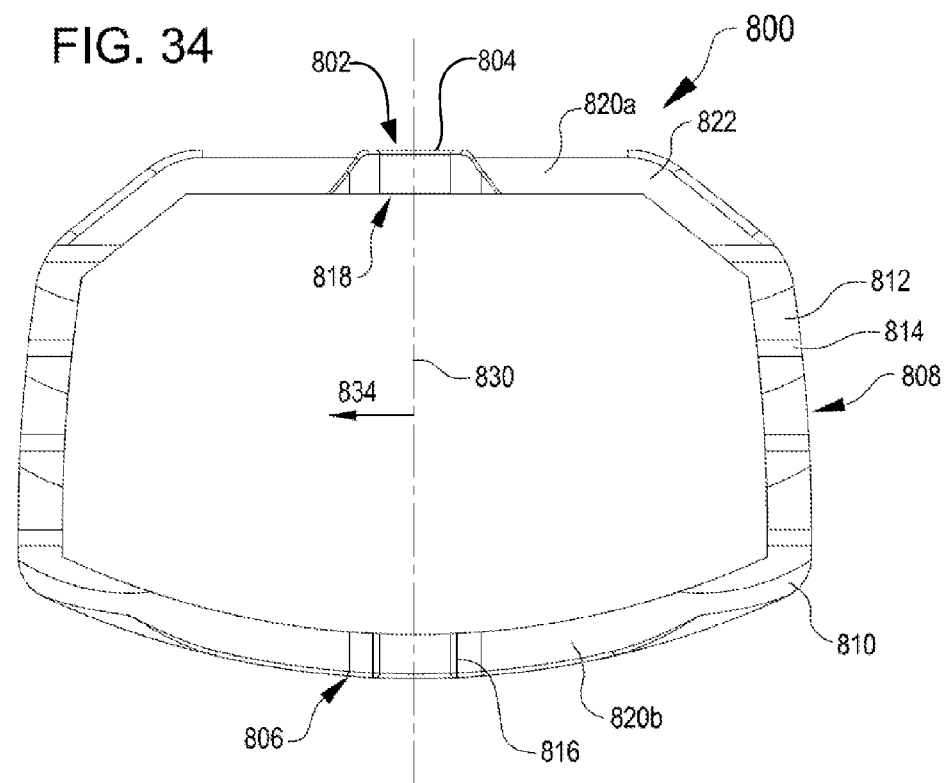

FIG. 34 shows the intervertebral implant 800 of FIG. 33 in a top view. The top view more clearly shows the blunt anterior surface 804 of the implant 800. The wings 808 expand away from the central axis 830 in horizontal direction 834 from the anterior end element 802 to the posterior end 806. Also shown more clearly is the curvature of the posterior structural elements 820b, which join with the posterior end 806.

Figure 35:
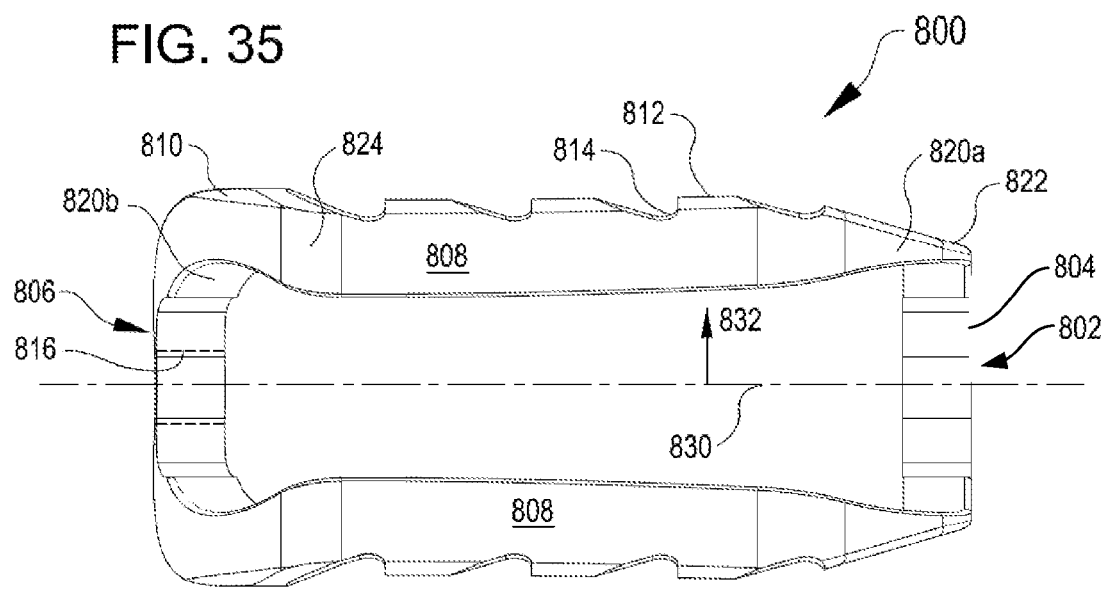

FIG. 35 shows the intervertebral implant 800 of FIGS. 33-34 in a side view. The side view more clearly shows the sloped anterior shoulders 822 of the implant 800 defining a surface of the anterior end element 802 and the anterior structural elements 820a. The anterior shoulders 822 are configured to help facilitate insertion of the implant in an intervertebral space in a patient's lumbar spine.

Figure 36:
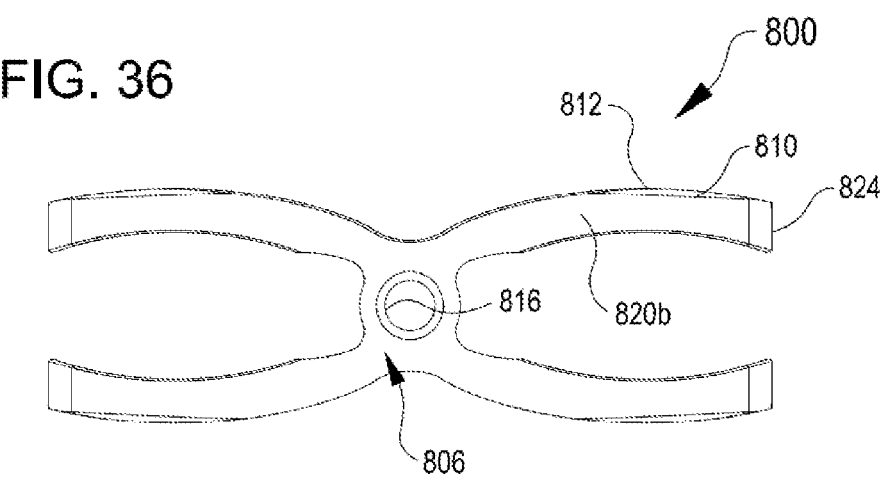

FIG. 36 shows the intervertebral implant 800 of FIGS. 33-35 in a posterior view. The posterior view more clearly shows the wing-like curvatures of the posterior structural elements 820b (and, by extension, the anterior structural elements 820a, FIGS. 33-35). The posterior view also more clearly shows a large volume of empty space surrounding the implant 800 for receiving graft material when the implant is installed in an intervertebral space in a patient.

Figure 37:
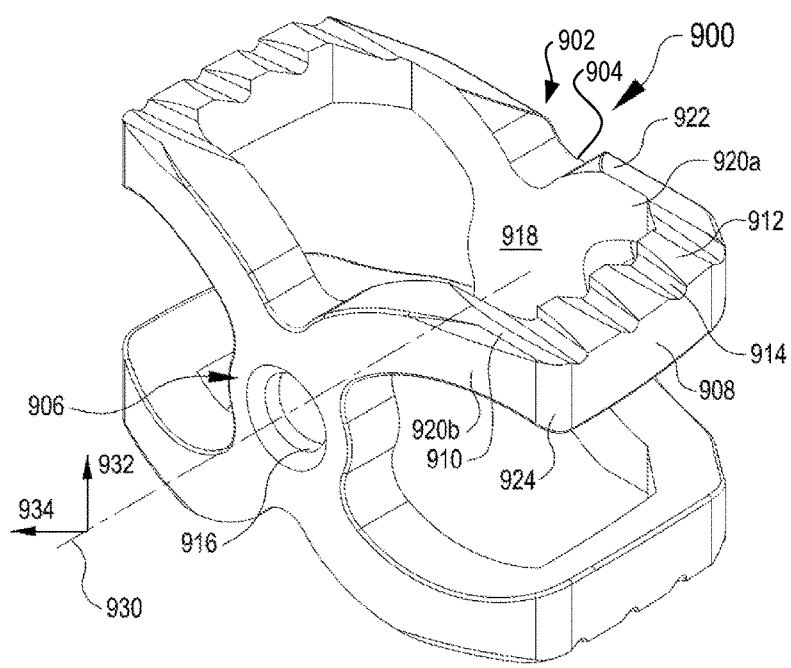
FIGS. 37-40 show a ninth example of an intervertebral fusion implant having a narrow aspect ratio, including: a perspective view (FIG. 37), a top view (FIG. 38), a side view (FIG. 39), and a posterior view (FIG. 40).

FIG. 37 shows a ninth intervertebral implant 900 in a perspective view. The implant 900 has an anterior end element 902 comprising a blunt anterior surface 904 and a narrow aspect ratio configured for facilitating insertion of the implant in the cervical spine of a patient in an ACIF procedure. The anterior end element 902 is positioned opposite a posterior end 906. A central axis 930 runs through the implant 900, orthogonal to a vertical direction 932 and a horizontal direction 934. The anterior surface 904 connects with sloped anterior shoulders 922 configured for facilitating ease of installation of the implant 900 in an intervertebral space. As with the first implant 100, the wings 908, the anterior end element 902, and the posterior end 906 define a substantially open space therebetween along the central axis 930.

Four wings 908 join the anterior end element 902 and the posterior end 906 via anterior and posterior structural members 920a, 920b. The wings 908 originate at the anterior structural members 920a and terminate with a curved shoulder 924 at the posterior structural members 920b. Each of the two top wings 908 has an outer surface 910 pointing upward in the vertical direction 932 and each of the two bottom wings 908 has an outer surface 910 pointing downward in the vertical direction 932. Each wing outer surface 910 has alternating teeth 912 and grooves 914. The posterior end 906 of the implant 900 has a cylindrical cavity 916 therethrough. The cylindrical cavity 916 can include attaching features for an installation tool, such as but not limited to, threads, notches, grooves, or other positive or negative surface features. Opposite the blunt anterior surface 904 at the anterior end element 902 of the implant 900, a rearward-facing inner surface 918 faces toward the cylindrical cavity 916.

Figure 38:
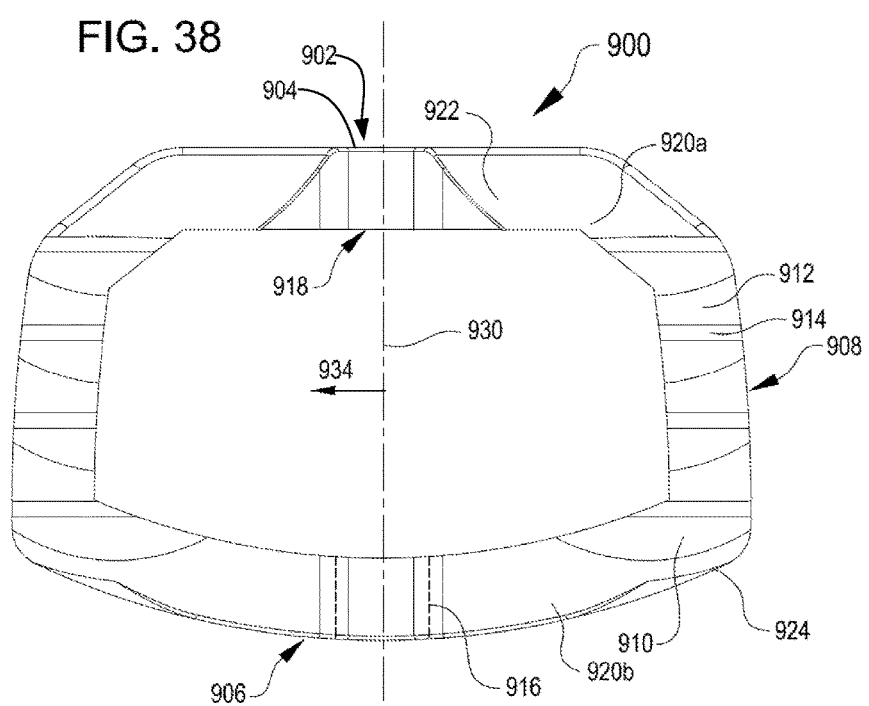

FIG. 38 shows the intervertebral implant 900 of FIG. 37 in a top view. The top view more clearly illustrates the blunt anterior surface 904 of the implant 900, and the blunt rearward-facing inner surface 918 of the anterior end element 902. The top view also shows the wings 908 extending horizontally away from the central axis 930 from the anterior end element 902 to the posterior end 906 of the implant 900. The curvatures of the posterior structural elements 920b are also shown as the posterior structural elements 920b connect with the posterior end 906.

Figure 39:
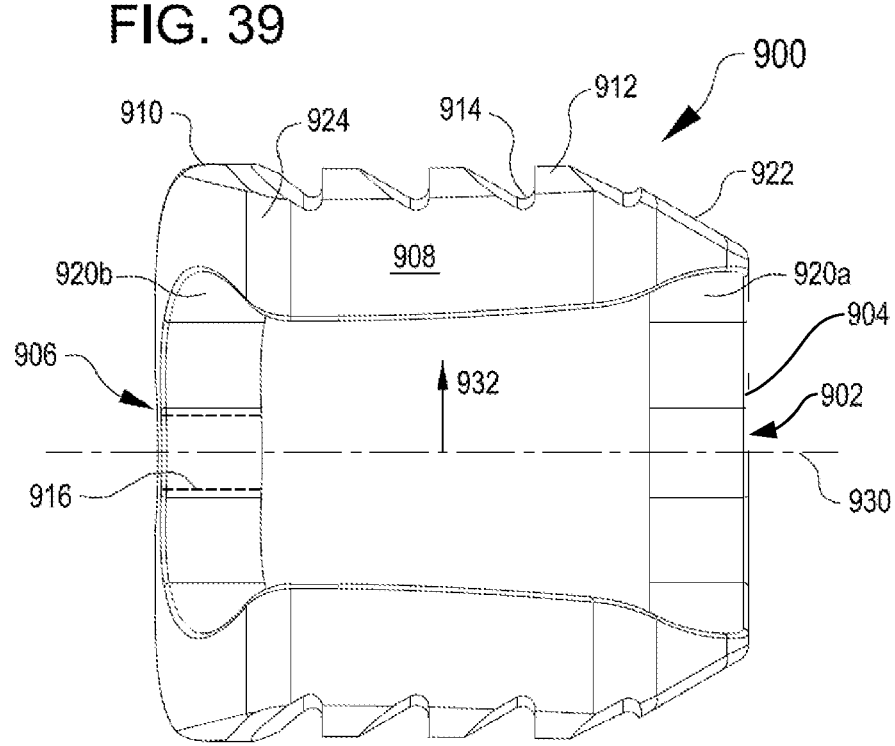

FIG. 39 shows the intervertebral implant 900 of FIGS. 37-38 in a side view. The side view more clearly illustrates the sloped surfaces of the anterior shoulders 922 of the anterior end element 902 and the anterior structural elements 920a. The anterior shoulders 922 are configured to aid in inserting the implant 900 in an intervertebral space in a patient's cervical spine.

Figure 40:
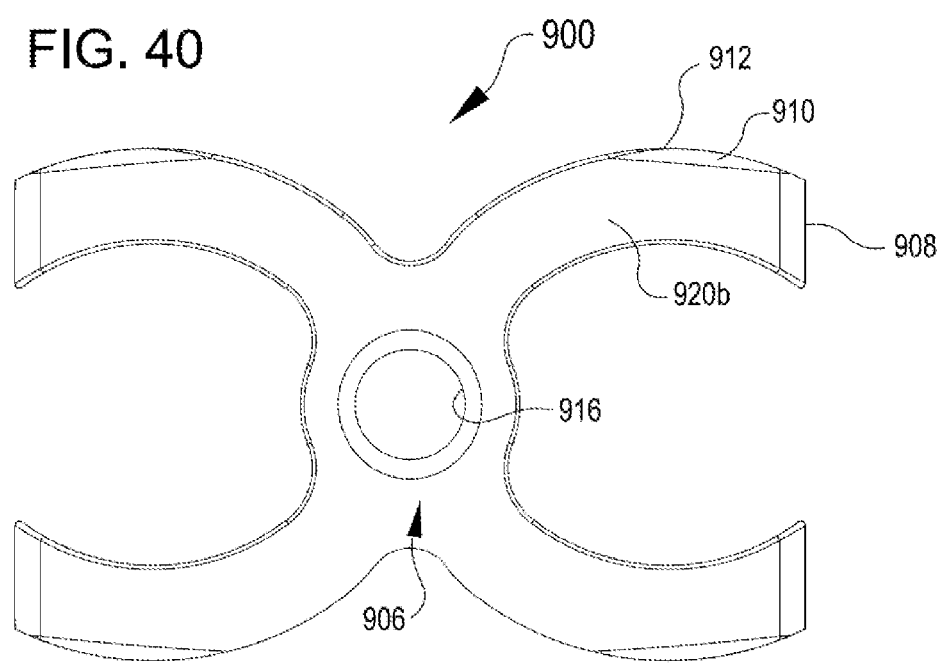

FIG. 40 shows the intervertebral implant 900 of FIGS. 37-39 in a posterior view. The posterior view more clearly illustrates the wing-like shapes of the posterior structural elements 920b (and, by extension, the anterior structural elements 920a (FIGS. 37-39)). The posterior view also shows more clearly the substantial open space provided surrounding the implant 900 for receiving graft material when the implant is installed in an intervertebral space in a patient.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An intervertebral implant, comprising:
an anterior end element having a cross-sectional area that increases in a direction from an anterior end of the implant toward a posterior end of the implant along a central axis of the implant;
four wings extending from the anterior end element in the direction of the posterior end, generally parallel to the central axis, and defining a substantially open space; and
a posterior end element at the posterior end connected with the four wings, wherein each of a first two of the four wings have a plurality of teeth configured to abut a first plane and each of a second two of the four wings have a plurality of teeth configured to abut a second plane parallel and spaced apart from the first plane, the first and second planes being parallel to a third plane containing the central axis of the implant; and
four posterior support members connected between the posterior end element and each one of the four wings, each of the four posterior support members being arranged to act as a cantilevered spring; wherein the four wings are not connected with each other between the anterior and posterior end elements.

2. The intervertebral implant of claim 1, further comprising a rearward-facing element adjacent the anterior end element and facing the posterior end, wherein the rearward-facing element narrows in a direction from the anterior end to the posterior end.

3. The intervertebral implant of claim 2, wherein the rearward-facing element is configured for spreading bone graft material when bone graft material is inserted around the implant.

4. The intervertebral implant of claim 1, further comprising:
four anterior support members connected between the anterior end element and each one of the four wings, each of the four anterior support members being arranged to act as a cantilevered spring.

5. The intervertebral implant of claim 1, wherein each of the four wings comprises an arc defined by at least some of the plurality of teeth, each of the arcs being convex in a direction away from the third plane containing the central axis of the implant.

6. The intervertebral implant of claim 1, wherein the four wings extend from equidistant points around a periphery of the anterior end element.

7. The intervertebral implant of claim 1, wherein the anterior end element is a contiguous anterior end element.

8. An intervertebral implant, comprising:
an anterior end element at an anterior end of the intervertebral implant;
a posterior end aligned with the anterior end element along a central axis of the intervertebral implant and separated from the anterior end element;
a posterior end element at the posterior end of the intervertebral implant and
four wings extending laterally between the anterior end element and the posterior end element, wherein:

an outer surface of each of the four wings comprises a plurality of grooves and a plurality of teeth;

the anterior end element, the posterior end element, and the four wings define a substantially open space therebetween;

each wing of the four wings is connected by at least one respective structural element of a plurality of structural elements, each respective structural element of the plurality of structural elements being arranged to act as a cantilevered spring; and wherein the four wings are not connected with each other between the anterior and posterior end elements.

9. The intervertebral implant of claim 8, wherein each wing of the four wings is connected with at least one of the anterior end element and the posterior end element.

10. The intervertebral implant of claim 8, further comprising:

a rear-facing element extending from the anterior end element and arranged within the substantially open space, the rear-facing element having a narrowing cross-sectional area from the anterior end element in the direction of the posterior end of the implant.

11. The intervertebral implant of claim 10, wherein: the rear-facing element comprises one of a cone, a pyramidal cone, or a divider, and wherein the rear-facing element is configured for spreading bone graft material when bone graft material is inserted in the implant within a patient.

12. The intervertebral implant of claim 8, wherein the anterior end element comprises a blunt anterior face, and wherein a shoulder of the intervertebral implant proximal to the anterior end element is sloped to facilitate surgical installation of the intervertebral implant.

13. The intervertebral implant of claim 8, wherein each of the four wings further comprises a surface roughness.

14. The intervertebral implant of claim 8, wherein at least some of the plurality of teeth further comprises a surface roughness.

15. The intervertebral implant of claim 8, wherein each of the four wings at least partially comprise a shape-memory material configured to plastically bend into a compressed shape and revert to an expanded shape.

16. The intervertebral implant of claim 8, wherein the anterior end element comprises a cross sectional area that increases in from the anterior end toward the posterior end along the central axis of the implant.

17. The intervertebral implant of claim 8, wherein the anterior end element further comprises an anterior cone that widens from a tip of the anterior end element toward the posterior end of the intervertebral implant, and further comprises one or more structural shoulders that connect the anterior end element with each of the four wings.

18. The intervertebral implant of claim 17, wherein the anterior end element comprises one of a round cone, a square pyramidal cone, or a wedge.

19. The intervertebral implant of claim 8, wherein:

the four wings comprise two inner wings spaced apart from two outer wings; and the central axis of the intervertebral implant comprises a curve along a horizontal plane, such that each of the two outer wings is longer than each of the two inner wings.

20. The intervertebral implant of claim 8, wherein:

a first portion of the anterior end element has a first anterior shoulder and a second portion of the anterior end element has a second anterior shoulder; and the first and second anterior shoulders are sloped, such that the first and second anterior shoulders extend away from the central axis from the anterior end of the intervertebral implant toward the posterior end of the intervertebral implant.

21. The intervertebral implant of claim 8, wherein the plurality of structural elements comprises a plurality of anterior structural members and a plurality of posterior structural members;

each wing of the four wings is connected with the anterior end element by a respective anterior structural member of the plurality of anterior structural members; and each wing of the four wings is connected with the posterior end element by a respective posterior structural member of the plurality of posterior structural members.

22. The intervertebral implant of claim 8, wherein:

each wing of the four wings has a respective curvature in a vertical direction relative to and away from the central axis of the intervertebral implant between the anterior and posterior ends.

23. The intervertebral implant of claim 22, wherein each wing of the four wings is flexible such that the respective curvature of each wing can substantially flatten when the intervertebral implant is installed in an intervertebral space in a patient.

24. The intervertebral implant of claim 8, wherein the anterior end element comprises an anterior cone facing an anterior direction from the intervertebral implant and that is configured to facilitate insertion of the intervertebral implant in an intervertebral space in a patient.

25. The intervertebral implant of claim 8, wherein the intervertebral implant is formed of a material having a stiffness of between 10 and 100 GPa.

26. The intervertebral implant of claim 8, wherein:

each wing of the four wings has a respective slope in a vertical direction relative to the central axis of the intervertebral implant between the anterior end and the posterior end.

27. The intervertebral implant of claim 8, wherein:

each wing of the four wings converge toward the central axis from the anterior end to the posterior end.

* * * * *